US011278671B2

United States Patent
Cavendish, Jr. et al.

(10) Patent No.: US 11,278,671 B2
(45) Date of Patent: Mar. 22, 2022

(54) INFUSION PUMP WITH SAFETY SEQUENCE KEYPAD

(71) Applicant: ICU Medical, Inc., San Clemente, CA (US)

(72) Inventors: Dirceu Galvao Cavendish, Jr., San Clemente, CA (US); Diego Andres Kaplan, San Clemente, CA (US); James Cudney, San Clemente, CA (US); Kerin Leigh Klagges-Kingsbury, San Clemente, CA (US)

(73) Assignee: ICU Medical, Inc., San Clemente, CA (US)

( * ) Notice: Subject to any disclaimer, the term of this patent is extended or adjusted under 35 U.S.C. 154(b) by 285 days.

(21) Appl. No.: 16/703,756

(22) Filed: Dec. 4, 2019

(65) Prior Publication Data

US 2021/0170101 A1    Jun. 10, 2021

(51) Int. Cl.
*A61M 5/172* (2006.01)
*G16H 20/17* (2018.01)
*G16H 40/63* (2018.01)

(52) U.S. Cl.
CPC ............ *A61M 5/172* (2013.01); *G16H 20/17* (2018.01); *G16H 40/63* (2018.01);
(Continued)

(58) Field of Classification Search
CPC ........ G16H 20/17; G16H 40/63; G16H 10/60; G16H 40/67; G16H 20/10; A61M 5/172;
(Continued)

(56) References Cited

U.S. PATENT DOCUMENTS

| 3,401,337 A | 9/1968 | Beusman et al. |
| 3,484,681 A | 12/1969 | Grady, Jr. et al. |

(Continued)

FOREIGN PATENT DOCUMENTS

| AU | 2013216679 | 9/2013 |
| BR | PI0704229-9 | 11/2009 |

(Continued)

OTHER PUBLICATIONS

Daimiwal et al., "Wireless Transfusion Supervision and Analysis Using Embedded System", IEEE, 2010 International Conference ICBBT, China, Apr. 2010, pp. 56-60.
(Continued)

*Primary Examiner* — Manuel A Mendez
(74) *Attorney, Agent, or Firm* — Knobbe, Martens, Olson & Bear, LLP

(57) ABSTRACT

An infusion pump is configured to provide one or more context cues to a user while the user programs the infusion pump to deliver an infusion therapy. In some embodiments, the infusion pump includes a display configured to display a keypad and to receive input from a user, a processor in communication with the display, and a memory in communication with the processor. The memory stores instructions that cause a keypad sequence monitor to receive context parameters, the context parameters corresponding to a drug selection, a drug concentration selection, or a clinical care area in which the drug is to be infused. The keypad sequence monitor accesses a drug library using the context parameter to determine a valid parameter range corresponding to a range of values between lower and upper soft limit values stored in the drug library. The keypad sequence monitor is further configured to receive an treatment parameter value from the user and display one or more context cues upon determining that the received treatment parameter value is
(Continued)

outside of a valid treatment parameter range, but would be within a valid treatment parameter range if one of the context parameters were changed.

20 Claims, 9 Drawing Sheets

(52) U.S. Cl.
CPC . *A61M 2205/3584* (2013.01); *A61M 2205/50* (2013.01); *A61M 2205/505* (2013.01); *A61M 2205/52* (2013.01); *A61M 2205/584* (2013.01); *A61M 2205/6054* (2013.01); *A61M 2205/6072* (2013.01)

(58) Field of Classification Search
CPC ................ A61M 5/1723; A61M 5/142; A61M 5/14244; A61M 5/14276; A61B 5/14532
See application file for complete search history.

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,894,431 A | 7/1975 | Muston et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |

(56) References Cited

U.S. PATENT DOCUMENTS

| | | |
|---|---|---|
| 4,521,212 A | 6/1985 | Ruschke |
| 4,525,163 A | 6/1985 | Slavik et al. |
| 4,526,568 A | 7/1985 | Clemens et al. |
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Bloomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,014,798 A | 5/1991 | Glynn |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |

(56) References Cited

U.S. PATENT DOCUMENTS

| | | |
|---|---|---|
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,260,665 A | 11/1993 | Goldberg |
| 5,257,206 A | 12/1993 | Hanson |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,304,216 A | 4/1994 | Wallace |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |

(56) References Cited

U.S. PATENT DOCUMENTS

| | | |
|---|---|---|
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A | 5/1997 | Feldman et al. |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |

(56) References Cited

U.S. PATENT DOCUMENTS

| | | |
|---|---|---|
| 5,954,696 A | 9/1999 | Ryan et al. |
| 5,956,023 A | 9/1999 | Lyle et al. |
| 5,956,501 A | 9/1999 | Brown |
| 5,957,885 A | 9/1999 | Bollish et al. |
| 5,957,890 A | 9/1999 | Mann et al. |
| 5,971,594 A | 10/1999 | Sahai et al. |
| 5,973,497 A | 10/1999 | Bergk et al. |
| 5,975,081 A | 11/1999 | Hood et al. |
| 5,989,222 A | 11/1999 | Cole et al. |
| 5,990,838 A | 11/1999 | Burns et al. |
| 5,991,525 A | 11/1999 | Shah et al. |
| 5,993,393 A | 11/1999 | Ryan et al. |
| 5,994,876 A | 11/1999 | Canny et al. |
| 5,997,476 A | 12/1999 | Brown |
| 6,000,828 A | 12/1999 | Leet |
| 6,003,006 A | 12/1999 | Colella et al. |
| 6,003,388 A | 12/1999 | Oeftering |
| 6,012,034 A | 1/2000 | Hamparian et al. |
| 6,017,318 A | 1/2000 | Gauthier et al. |
| 6,017,493 A | 1/2000 | Cambron |
| 6,021,392 A | 2/2000 | Lester et al. |
| 6,023,977 A | 2/2000 | Langdon et al. |
| 6,024,539 A | 2/2000 | Blomquist |
| 6,027,441 A | 2/2000 | Cantu |
| 6,028,412 A | 2/2000 | Shine et al. |
| 6,032,676 A | 3/2000 | Moore |
| 6,033,561 A | 3/2000 | Schoendorfer |
| 6,036,017 A | 3/2000 | Bayliss, IV |
| 6,068,612 A | 5/2000 | Bowman |
| 6,068,615 A | 5/2000 | Brown et al. |
| 6,073,106 A | 6/2000 | Rozen et al. |
| 6,077,246 A | 6/2000 | Kullas et al. |
| 6,083,206 A | 7/2000 | Molko |
| 6,089,104 A | 7/2000 | Chang |
| 6,104,295 A | 8/2000 | Gaisser et al. |
| 6,110,152 A | 8/2000 | Kovelman |
| 6,110,153 A | 8/2000 | Davis |
| RE36,871 E | 9/2000 | Epstein et al. |
| 6,120,459 A | 9/2000 | Nitzan et al. |
| 6,122,536 A | 9/2000 | Sun et al. |
| 6,142,008 A | 11/2000 | Cole et al. |
| 6,150,942 A | 11/2000 | O'Brien |
| 6,157,914 A | 12/2000 | Seto et al. |
| 6,158,288 A | 12/2000 | Smith |
| 6,158,965 A | 12/2000 | Butterfield et al. |
| 6,159,147 A | 12/2000 | Lichter et al. |
| 6,159,186 A | 12/2000 | Wickham et al. |
| 6,164,921 A | 12/2000 | Moubayed et al. |
| 6,168,561 B1 | 1/2001 | Cantu |
| 6,178,827 B1 | 1/2001 | Feller |
| 6,182,667 B1 | 2/2001 | Hanks et al. |
| 6,186,141 B1 | 2/2001 | Pike et al. |
| 6,189,105 B1 | 2/2001 | Lopes |
| 6,192,752 B1 | 2/2001 | Blaine |
| 6,195,589 B1 | 2/2001 | Ketcham |
| 6,202,711 B1 | 3/2001 | Martucci |
| 6,203,528 B1 | 3/2001 | Deckert |
| 6,208,107 B1 | 3/2001 | Maske et al. |
| 6,212,936 B1 | 4/2001 | Meisberger |
| 6,213,972 B1 | 4/2001 | Butterfield |
| 6,231,320 B1 | 5/2001 | Lawless et al. |
| 6,234,176 B1 | 5/2001 | Domae et al. |
| 6,236,326 B1 | 5/2001 | Murphy et al. |
| 6,237,398 B1 | 5/2001 | Porat et al. |
| 6,241,704 B1 | 6/2001 | Peterson et al. |
| 6,248,067 B1 | 6/2001 | Causey, III et al. |
| 6,250,132 B1 | 6/2001 | Drzewiecki |
| 6,259,355 B1 | 7/2001 | Chaco et al. |
| 6,259,587 B1 | 7/2001 | Sheldon et al. |
| 6,261,065 B1 | 7/2001 | Nayak |
| 6,262,946 B1 | 7/2001 | Khuri-Yakub et al. |
| 6,267,559 B1 | 7/2001 | Mossman et al. |
| 6,267,725 B1 | 7/2001 | Dubberstein et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,277,099 B1 | 8/2001 | Strowe et al. |
| 6,280,380 B1 | 8/2001 | Bardy |
| 6,280,391 B1 | 8/2001 | Olson et al. |
| 6,280,408 B1 | 8/2001 | Sipin |
| 6,283,761 B1 | 9/2001 | Joao |
| 6,285,155 B1 | 9/2001 | Maske et al. |
| 6,312,378 B1 | 11/2001 | Bardy |
| 6,322,516 B1 | 11/2001 | Masuda et al. |
| 6,330,351 B1 | 12/2001 | Yasunaga |
| 6,337,675 B1 | 1/2002 | Toffolo et al. |
| 6,345,539 B1 | 2/2002 | Rawes et al. |
| 6,347,553 B1 | 2/2002 | Morris et al. |
| 6,349,740 B1 | 2/2002 | Cho et al. |
| 6,358,225 B1 | 3/2002 | Butterfield |
| 6,358,387 B1 | 3/2002 | Kopf-Sill et al. |
| 6,362,591 B1 | 3/2002 | Moberg |
| 6,385,505 B1 | 5/2002 | Lipps |
| 6,386,050 B1 | 5/2002 | Yin et al. |
| 6,394,958 B1 | 5/2002 | Bratteli et al. |
| 6,396,583 B1 | 5/2002 | Clare |
| 6,398,760 B1 | 6/2002 | Danby |
| 6,405,076 B1 | 6/2002 | Taylor et al. |
| 6,408,679 B1 | 6/2002 | Kline-Schoder et al. |
| 6,413,238 B1 | 7/2002 | Maget |
| 6,416,291 B1 | 7/2002 | Butterfield et al. |
| 6,418,334 B1 | 7/2002 | Unger et al. |
| 6,418,535 B1 | 7/2002 | Kulakowski et al. |
| 6,445,053 B1 | 9/2002 | Cho |
| 6,456,245 B1 | 9/2002 | Crawford |
| 6,457,346 B1 | 10/2002 | Kline-Schoder et al. |
| 6,463,785 B1 | 10/2002 | Kline-Schoder et al. |
| 6,467,331 B1 | 10/2002 | Kline-Schoder et al. |
| 6,468,242 B1 | 10/2002 | Wilson et al. |
| 6,475,178 B1 | 11/2002 | Krajewski |
| 6,481,980 B1 | 11/2002 | Vandlik |
| 6,482,158 B2 | 11/2002 | Mault |
| 6,482,185 B1 | 11/2002 | Hartmann |
| 6,485,263 B1 | 11/2002 | Bryant et al. |
| 6,485,418 B2 | 11/2002 | Yasushi et al. |
| 6,485,465 B2 | 11/2002 | Moberg et al. |
| 6,487,916 B1 | 12/2002 | Gomm et al. |
| 6,489,896 B1 | 12/2002 | Platt |
| 6,494,694 B2 | 12/2002 | Lawless et al. |
| 6,494,831 B1 | 12/2002 | Koritzinsky |
| 6,497,680 B1 | 12/2002 | Holst et al. |
| 6,503,221 B1 | 1/2003 | Briggs |
| 6,512,944 B1 | 1/2003 | Kovtun et al. |
| 6,516,667 B1 | 2/2003 | Broad et al. |
| 6,517,482 B1 | 2/2003 | Eiden et al. |
| 6,519,569 B1 | 2/2003 | White et al. |
| 6,529,751 B1 | 3/2003 | Van Driel et al. |
| 6,531,708 B1 | 3/2003 | Malmstrom |
| 6,539,315 B1 | 3/2003 | Adams et al. |
| 6,540,672 B1 | 4/2003 | Simonsen et al. |
| 6,544,212 B2 | 4/2003 | Galley et al. |
| 6,544,228 B1 | 4/2003 | Heitmeier |
| 6,558,125 B1 | 5/2003 | Futterknecht |
| 6,558,351 B1 | 5/2003 | Steil et al. |
| 6,562,012 B1 | 5/2003 | Brown et al. |
| 6,564,825 B2 | 5/2003 | Lowery et al. |
| 6,565,509 B1 | 5/2003 | Say et al. |
| 6,568,416 B2 | 5/2003 | Tucker et al. |
| 6,572,542 B1 | 6/2003 | Houben et al. |
| 6,572,545 B2 | 6/2003 | Knobbe et al. |
| 6,572,576 B2 | 6/2003 | Brugger et al. |
| 6,578,422 B2 | 6/2003 | Lam et al. |
| 6,578,435 B2 | 6/2003 | Gould et al. |
| 6,581,117 B1 | 6/2003 | Klein et al. |
| RE38,189 E | 7/2003 | Walker et al. |
| 6,585,675 B1 | 7/2003 | O'Mahony et al. |
| 6,589,229 B1 | 7/2003 | Connelly et al. |
| 6,589,792 B1 | 7/2003 | Malachowski |
| 6,599,281 B1 | 7/2003 | Struys et al. |
| 6,599,282 B2 | 7/2003 | Burko |
| 6,602,191 B2 | 8/2003 | Quy |
| 6,605,072 B2 | 8/2003 | Struys et al. |
| 6,606,047 B1 | 8/2003 | Börjesson et al. |

(56) References Cited

U.S. PATENT DOCUMENTS

| | | |
|---|---|---|
| 6,609,047 B1 | 8/2003 | Lipps |
| 6,615,674 B2 | 9/2003 | Ohnishi |
| 6,616,633 B1 | 9/2003 | Butterfield et al. |
| 6,617,564 B2 | 9/2003 | Ockerse et al. |
| 6,618,916 B1 | 9/2003 | Eberle et al. |
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouda et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Gimdt |

(56) References Cited

U.S. PATENT DOCUMENTS

| | | |
|---|---|---|
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |
| 7,338,470 B2 | 3/2008 | Katz |
| 7,347,836 B2 | 3/2008 | Peterson et al. |
| 7,347,854 B2 | 3/2008 | Shelton et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,605,730 B2 | 10/2009 | Tomioka et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenskow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,976,508 B2 | 7/2011 | Hoag |
| 7,981,073 B2 | 7/2011 | Mollstam |
| 7,981,082 B2 | 7/2011 | Wang et al. |
| 8,002,736 B2 | 8/2011 | Patrick et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,514 B2 | 12/2011 | Butterfield et al. |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blornquist |
| 8,175,668 B1 | 5/2012 | Nabutovsky et al. |
| 8,177,739 B2 | 5/2012 | Cartledge et al. |
| 8,180,440 B2 | 5/2012 | McCombie et al. |
| 8,185,322 B2 | 5/2012 | Schroeder et al. |
| 8,219,413 B2 | 7/2012 | Martinez et al. |
| 8,221,395 B2 | 7/2012 | Shelton et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,449,524 B2 | 5/2013 | Braig et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,523,797 B2 | 9/2013 | Lowery et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,905,965 B2 | 12/2014 | Mandro et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| 9,190,010 B2 | 11/2015 | Vik et al. |
| 9,240,002 B2 | 1/2016 | Hume et al. |
| 9,272,089 B2 | 3/2016 | Jacobson et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,545,475 B2 | 1/2017 | Borges et al. |
| 9,707,341 B2 | 7/2017 | Dumas, III et al. |
| 9,764,087 B2 | 9/2017 | Peterfreund et al. |
| 9,852,265 B1 | 12/2017 | Treacy et al. |
| 9,943,269 B2 | 4/2018 | Muhsin et al. |

(56) References Cited

U.S. PATENT DOCUMENTS

| | | |
|---|---|---|
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,166,328 B2 | 1/2019 | Oruklu et al. |
| 10,342,917 B2 | 7/2019 | Shubinsky et al. |
| 10,430,761 B2 | 10/2019 | Hume et al. |
| 10,463,788 B2 | 11/2019 | Day |
| 10,549,248 B2 | 2/2020 | Brown et al. |
| 10,578,474 B2 | 3/2020 | Ruchti et al. |
| 10,596,316 B2 | 3/2020 | Dumas, III et al. |
| 10,635,784 B2 | 4/2020 | Rubalcaba, Jr. et al. |
| 10,656,894 B2 | 5/2020 | Fryman |
| 10,682,102 B2 | 6/2020 | Declerck |
| 10,850,024 B2 | 12/2020 | Day et al. |
| 10,874,793 B2 | 12/2020 | Oruklu et al. |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1 | 4/2002 | Baker, Jr. et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018289 A1 | 1/2003 | Ng et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0186833 A1 | 10/2003 | Huff et al. |
| 2003/0187338 A1 | 10/2003 | Say et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0216682 A1 | 11/2003 | Junker |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0128162 A1 | 7/2004 | Schlotterbeck et al. |
| 2004/0128163 A1 | 7/2004 | Goodman et al. |
| 2004/0133166 A1 | 7/2004 | Moberg et al. |
| 2004/0145114 A1 | 7/2004 | Ippolito et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0108057 A1 | 5/2005 | Cohen et al. |
| 2005/0119597 A1 | 6/2005 | O'Mahony et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |

(56) References Cited

U.S. PATENT DOCUMENTS

| | | |
|---|---|---|
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0197649 A1 | 9/2005 | Shelton et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136095 A1 | 6/2006 | Rob et al. |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224140 A1 | 10/2006 | Junker |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229918 A1 | 10/2006 | Fotsch et al. |
| 2006/0235353 A1 | 10/2006 | Gelfand et al. |
| 2006/0255149 A1 | 11/2006 | Retter et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0094045 A1 | 4/2007 | Cobbs et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0179436 A1 | 8/2007 | Braig et al. |
| 2007/0191817 A1 | 8/2007 | Martin |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0250339 A1 | 10/2007 | Mallett et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0105636 A1 | 4/2009 | Hayter et al. |

(56) References Cited

U.S. PATENT DOCUMENTS

| | | |
|---|---|---|
| 2009/0112155 A1 | 4/2009 | Zhao |
| 2009/0114037 A1 | 5/2009 | Smith |
| 2009/0119330 A1 | 5/2009 | Sampath et al. |
| 2009/0124963 A1 | 5/2009 | Hogard et al. |
| 2009/0124964 A1 | 5/2009 | Leach et al. |
| 2009/0126825 A1 | 5/2009 | Eliuk et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0057042 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0114027 A1 | 5/2010 | Jacobson et al. |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0185182 A1 | 7/2010 | Alme et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0217154 A1 | 8/2010 | Deshmukh et al. |
| 2010/0217621 A1 | 8/2010 | Schoenberg |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0317093 A1 | 12/2010 | Turewicz et al. |
| 2010/0317952 A1 | 12/2010 | Budiman et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0107251 A1 | 5/2011 | Guaitoli et al. |
| 2011/0137241 A1 | 6/2011 | DelCastilio et al. |
| 2011/0144595 A1 | 6/2011 | Cheng |
| 2011/0152770 A1 | 6/2011 | Diperna et al. |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0218514 A1 | 9/2011 | Rebours |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0313390 A1 | 12/2011 | Roy et al. |
| 2011/0319728 A1 | 12/2011 | Petisce et al. |
| 2011/0320049 A1 | 12/2011 | Chossat et al. |
| 2012/0025995 A1 | 2/2012 | Moberg et al. |
| 2012/0059234 A1 | 3/2012 | Barrett et al. |
| 2012/0068001 A1 | 3/2012 | Pushkarsky et al. |
| 2012/0083760 A1 | 4/2012 | Ledford et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2012/0310204 A1 | 12/2012 | Krogh et al. |
| 2012/0323212 A1 | 12/2012 | Murphy |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0041342 A1 | 2/2013 | Bernini et al. |
| 2013/0044111 A1 | 2/2013 | VanGilder et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0197930 A1 | 8/2013 | Garibaldi et al. |
| 2013/0201482 A1 | 8/2013 | Munro |
| 2013/0116649 A1 | 9/2013 | Kouyoumjian et al. |
| 2013/0253430 A1 | 9/2013 | Kouyoumjian et al. |
| 2013/0274576 A1 | 10/2013 | Amirouche et al. |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0345658 A1 | 12/2013 | Browne et al. |
| 2013/0345666 A1 | 12/2013 | Panduro et al. |
| 2014/0067425 A1 | 3/2014 | Dudar et al. |
| 2014/0180711 A1 | 6/2014 | Kamen et al. |
| 2014/0224829 A1 | 8/2014 | Capone et al. |
| 2014/0267563 A1 | 9/2014 | Baca et al. |
| 2014/0303591 A1 | 10/2014 | Peterfreund et al. |
| 2015/0025453 A1 | 1/2015 | Ledford et al. |
| 2015/0033073 A1 | 1/2015 | Yang et al. |
| 2015/0065988 A1 | 3/2015 | Holderle et al. |
| 2015/0168958 A1 | 6/2015 | Downie et al. |
| 2015/0343141 A1 | 12/2015 | Lindo et al. |
| 2016/0042264 A1 | 2/2016 | Borges et al. |

(56) References Cited

U.S. PATENT DOCUMENTS

| | | |
|---|---|---|
| 2016/0110088 A1 | 4/2016 | Vik et al. |
| 2016/0151560 A1 | 6/2016 | Toro et al. |
| 2016/0151562 A1 | 6/2016 | Magers et al. |
| 2016/0151601 A1 | 6/2016 | Cardelius et al. |
| 2016/0175517 A1 | 6/2016 | Sileika et al. |
| 2016/0193604 A1 | 7/2016 | McFarland et al. |
| 2016/0256622 A1 | 9/2016 | Day et al. |
| 2016/0339167 A1 | 11/2016 | Ledford et al. |
| 2017/0043089 A1 | 2/2017 | Handler |
| 2017/0354941 A1 | 12/2017 | Brown et al. |
| 2018/0018440 A1 | 1/2018 | Sugawara |
| 2019/0091401 A1 | 3/2019 | Ruchti et al. |
| 2019/0117890 A1 | 4/2019 | Oruklu et al. |
| 2019/0196770 A1 | 6/2019 | Fryman |
| 2019/0262535 A1 | 8/2019 | Shubinsky et al. |
| 2019/0282757 A1 | 9/2019 | Gylland et al. |
| 2020/0069864 A1 | 3/2020 | Shubinsky et al. |
| 2020/0090122 A1 | 3/2020 | Hume |
| 2020/0238007 A1 | 7/2020 | Day |
| 2020/0271499 A1 | 8/2020 | Ruchti et al. |
| 2020/0282137 A1 | 9/2020 | Dumas, III et al. |
| 2020/0319837 A1 | 10/2020 | Fryman |
| 2020/0324044 A1 | 10/2020 | Gylland et al. |
| 2020/0357500 A1 | 11/2020 | Rubalcaba, Jr. et al. |

FOREIGN PATENT DOCUMENTS

| | | |
|---|---|---|
| CA | 2 113 473 | 3/1993 |
| CA | 2 551 817 | 7/2005 |
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 1 490 131 | 12/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-518471 | 7/2007 |
| JP | 2007-520270 | 7/2007 |
| JP | 2007-275106 | 10/2007 |
| JP | 2008-249400 | 10/2008 |
| JP | 4322661 | 6/2009 |
| JP | 2010-063767 | 3/2010 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/070994 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |

(56) References Cited

FOREIGN PATENT DOCUMENTS

| | | |
|---|---|---|
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2009/141504 | 11/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2012/108910 | 8/2012 |
| WO | WO 2012/167090 | 12/2012 |
| WO | WO 2013/096769 | 6/2013 |
| WO | WO 2015/134478 | 9/2015 |
| WO | WO 2017/051271 | 3/2017 |
| WO | WO 2017/144366 | 8/2017 |
| WO | WO 2020/214717 | 10/2020 |

OTHER PUBLICATIONS

International Search Report and Written Opinion received in PCT Application No. PCT Application No. PCT/US2020/062741, dated Mar. 12, 2021 in 15 pages.
Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.
Alaris® Medical Systems, "Signature Edition® GOLD—Single & Dual Channel Infusion System", San Diego, CA, USA, date unknown, but believed to be at least as early as Nov. 29, 2008, pp. 70-74, 2-88 & 2-91.
Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-releases/2014/05_08_14_sigma.page.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Buhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
"Decision of the Administrative Council of Oct. 16, 2013 Amending Rule 135 and 164 of the Implementing Regulations to the European Patent Convention (CA/D 17/13)", Official Journal EPO Nov. 2013, Nov. 2013, pp. 503-506. http://archive.epo.org/epo/pubs/oj013/11_13/11_5033.pdf.
"Decision of the Administrative Council of Oct. 27, 2009 Amending the Implementing Regulations to the European Patent Convention (CA/D 20/09)", Official Journal EPO Dec. 2009, Dec. 2009, pp. 582-584. http://archive.epo.org/epo/pubs/oj009/12_09/12_5829.pdf.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", http://www.merriam-webster.com/dictionary/froth, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. www.hospira.com/products_and_services/infusion_pumps/plum/index.

(56) References Cited

OTHER PUBLICATIONS

Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.
Moghissi, Etie, MD, FACP, FACE, "Hyperglycemia in Hospitalized Patients", A Supplement to AGP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An *in Silico* Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.
Tang et al., "Linear Dimensionality Reduction Using Relevance Weighted LDA", Pattern Recognition, 2005, vol. 38, pp. 485-493, http://staff.ustc.edu.cn/~ketang/papers/TangSuganYaoQin_PR04.pdf.
Thomas et al., "Implementation of a Tight Glycaemic Control Protocol Using a Web-Based Insulin Dose Calculator", Anaesthesia, 2005, vol. 60, pp. 1093-1100.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Westbrook et al., "Errors in the Administration of Intravenous Medications in Hospital and the Role of Correct Procedures and Nurse Experience", BMJ Quality & Safety, 2011, vol. 20, pp. 1027-1034.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

INFUSION PUMP WITH SAFETY SEQUENCE KEYPAD

TECHNICAL FIELD

This disclosure relates to the field of infusion pumps, and particularly to techniques for monitoring data entry actions by a user to minimize errors as the user enters data to program an infusion pump treatment therapy.

BACKGROUND

Infusion pumps for infusing one or more fluids into a medical patient are commonplace in modern healthcare environments. Such infusion pumps may be programmed by a user to infuse a particular drug according to various treatment parameters, such as dose, rate, volume, and/or duration of time. A drug library accessed by the infusion pump defines safe settings and limits for each treatment parameter. The safe settings and limits may vary depending upon one or more context parameters, such as the clinical care area in which the pump is located, the drug being infused, etc. An incorrectly selected context parameter by the user may cause the pump to utilize an incorrect set of safe settings or limits for the selected drug to be infused. In addition, typical pumps do not indicate to a user whether an entered value is within a valid range until the user completes the entry of the invalid value and confirms the submission to the infusion pump. It would be helpful for the pump to notify the user as soon as possible as to whether the entered value is valid, to guide the user as to keypresses that would result in a valid value, and to guide the user as to whether changing one or more context parameters would results in the out-of-range invalid value becoming an in-range valid value.

SUMMARY

Various techniques for providing a safety sequence keypad (or keyboard) are described herein. Although many of the examples are described in the context of a networked hospital environment, the techniques described herein can be applied to any networked or non-networked environment. The infusion pumps described herein sometimes be other medical devices, or non-medical devices, or any combination thereof. In various embodiments, a safety sequence keypad of an infusion pump is configured to provide feedback to a user after each key is pressed on the pump's keypad. The infusion pump does not wait until the user completes entering and submits an entered value to provide feedback as to whether the value is valid or not. Instead, the safety sequence keypad is able to indicate, based upon selected context parameters, the drug library, and a partial sequence entered by the user, all subsequent key presses that can result in a valid treatment parameter entry. Such keypad advantageously enables real time feedback to a user during data entry. The features described herein help prevent delivery of incorrect therapies and reduce clinical errors. These and other embodiments are described in greater detail below with reference to FIGS. 1-6.

BRIEF DESCRIPTION OF THE DRAWINGS

The embodiments described herein are illustrated by way of example, and not by way of limitation, in the figures of the accompanying drawings in which like references indicate similar elements.

DETAILED DESCRIPTION

Introduction

Figure 1:
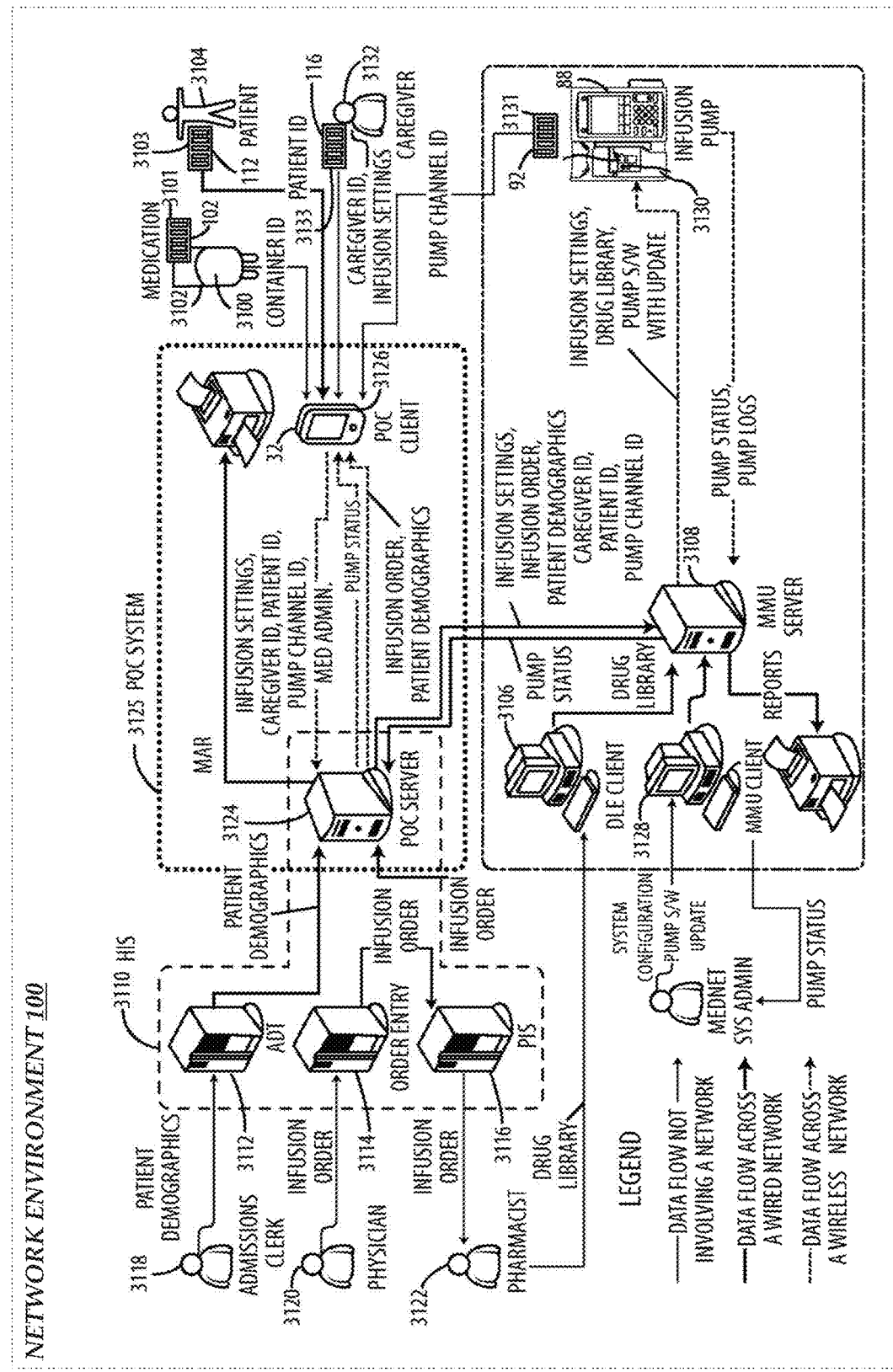
FIG. 1 is a schematic diagram of an example network environment including one or more networked infusion pumps in accordance with aspects of this disclosure.

An infusion pumps for infusing one or more fluids into a medical patient may be programmed by a user to infuse a particular drug according to various treatment parameters, such as dose, rate, volume, and/or duration of time. A drug library accessed by the infusion pump includes one or more rules that define predetermined safe ranges of values for the treatment parameters. For a given drug, the drug library may define lower and upper values of the treatment parameters that have been determined to be safe for use with the particular drug. The lower and upper values may be referred to as "soft limits." The range of values between the lower and upper soft limits define a safe range of values of the treatment parameter of interest. For a given drug, the drug library may also define lower and upper values of each treatment parameters that may not be exceeded by the user under any circumstance. These lower and upper values may be referred to as "hard limits." The pump will not allow the selection of a treatment parameter value that is below the lower hard limit or above the upper hard limit under any circumstance. Such rules are generally determined at least based upon the particular drug to be administered by the infusion pump. In addition, the rules for a given drug may vary based upon the concentration of the drug to be administered and/or the clinical care are of the hospital in which the drug is to be administered, and/or other drug library parameters.

The range of values between the soft and hard limits are values that may be selected by the user, but only after confirmation from the user that the user wishes to override the soft limit restriction. The pump keypad may provide the user with an override button for the user to provide such confirmation. Hard limit restrictions may not be overridden.

For example, a user may program a pump to deliver the drug dopamine (of a particular concentration, such as, for example, 400 mg/250 mL) to a medical patient. The pump may access a drug library and determine that the lower and upper hard limits for dosing this particular drug are 0 and 50 mcg/kg/min (micrograms of drug per kilogram of patient weight per minute). Therefore, the user will not be able to enter and submit a dosing value for this drug that is below 0 mcg/kg/min or above 50 mcg/kg/min. The user will not be able to override the hard limit restriction. The drug library may also indicate that the lower and upper soft limits for dosing this particular drug are 2.5 mcg/kg/min and 20 mcg/kg/min. Therefore, the user will not be able to enter and submit a dosing value for this drug that is below 2.5 mcg/kg/min or above 20 mcg/kg/min unless the user activates an override key to override the soft limit restriction. The user may enter and submit a value within the range defined by the lower and upper soft limits (e.g., between 2.5 mcg/kg/min and 20 mcg/kg/min) without restriction.

The user may program other treatment parameters, e.g., infusion rate, volume-to-be-infused ("VTBI"), and/or infusion duration in a similar manner. Selection of such treatment parameter values may be similarly restricted by lower and upper soft and hard limit values for each of such treatment parameters.

The drug library and/or the lower and upper soft and hard limit restrictions may be determined not only based upon the drug to be infused, but also based upon one or more context parameters. Such context parameters include, for example, the drug to be infused, the drug concentration, and/or the clinical care area in which the pump is located. The drug library that is utilized and/or the lower and upper soft and hard limit restrictions may vary based upon the any one or more of the context parameters, such as, for example, location of the infusion pump. If the infusion pump is located in a neonatal intensive care unit (NICU), for example, a drug library may be selected to provide smaller lower and upper soft and limit values for a drug than if the infusion pump were located at location in the hospital that provides treatment to grown adults.

In some cases, one or more of the context parameters may be incorrectly selected. For example, an infusion pump that was moved from one clinical care area (e.g., NICU) to another clinical care area (e.g., general floor) may not have had its clinical care area context parameter updated. As a result, the infusion pump may access an incorrect drug library or an incorrect portion of a drug library (e.g., in situations where a drug library includes soft and hard limit data for multiple CCAs administering the same drug under the same or different concentrations), such as a drug library (or drug library portion) that provides over- or under-restrictive hard and soft limits for a particular drug. As a result, the infusion pump could possibly indicate that an entered treatment parameter value (e.g., dose) is out of range when it is actually would be in range if the CCA context parameter value had been set to the correct value. In such cases it would be helpful for the infusion pump to indicate to the user whether changing a context parameter value, such as the clinical care area, would result in a change to the treatment parameter limits, such that the change to the treatment parameter limits would result in the entered treatment parameter value falling within a valid, acceptable range of treatment parameter values.

Overview of Analyzing User Input on a Keypress-by-Keypress Basis

In some implementations, an infusion pump described above receives and analyzes user input (e.g., user programming of the infusion pump) on a keypress-by-keypress basis. For example, the infusion pump analyzes each keypress (sometimes referred to as keystroke, input, etc.) and indicates to the user, based on the selected context parameters and the sequence of programming keypresses entered so far, whether a particular subsequent keypress will result in a valid or invalid treatment parameter value selection. Analyzing user input on such basis advantageously enables the pump to notify the user as early as possible as to whether an entered sequence represents a valid or invalid value with respect to the drug being delivered and selected context parameters.

For example, a value is typically entered by pressing a desired numerical sequence followed by an "ENTER" or "CONFIRM" key (or equivalent). Pressing the "CONFIRM" key causes the entered value to be submitted to the pump's processor for processing, such as, for example, to determine whether the value is valid, or not. If the value "15" is desired, the user would typically press the key "1" followed by the key "5" and then the "CONFIRM" key. Only after the "CONFIRM" key is pressed would a typical infusion pump then indicate whether the entered treatment parameter value (in this example, "15") is a valid or not (e.g., within the limits defined by the drug library for the selected drug). In contrast, embodiments described herein indicate to the user whether the value "1" is a valid value immediately after the key "1" is pressed. In addition, the infusion pump will indicate which subsequent keypresses would result in a valid treatment parameter value entry before the next key is pressed. Similarly, after the key "5" is pressed, the pump will indicate whether the sequence entered so far (e.g., "15" in this example) is a valid entry, even prior to the user pressing the "CONFIRM" key. This advantageously allows the user to avoid entering and submitting an invalid value, and avoids having the hospital system record that the user has tried to submit an invalid value. It also allows for avoidance or immediate user awareness of and correction of common data entry errors, such as "fat fingers," (when a user accidentally presses the incorrect key, such as a key adjacent to a desired key), accidental digit reversal before such data entry errors are submitted to the pump's processor for processing.

In addition, if the sequence of programming keypresses entered so far has resulted in an invalid treatment parameter value selection, the infusion pump display can also indicate to the user whether changing one or more context parameter settings would result in redefining the range of acceptable treatment parameter values such that the value entered would become within a valid range of treatment parameter values. For example, changing a context parameter could result in changing the drug library rule selected by the pump, which could result in different lower and upper soft and hard limit restrictions for a particular treatment parameter (e.g., dose, rate, volume-to-be-infused, infusion duration, etc.). Indications as to whether changing a particular context parameter setting would result in the entered treatment parameter value becoming a valid treatment parameter value are referred to as context cues. Techniques for analyzing keypresses on a keypress-by-keypress basis and providing context cues are described in greater detail below with reference to FIGS. 2-5.

With reference to FIG. 1, an example network environment in which one or more infusion pumps implementing one of the techniques of the present disclosure may be utilized is described. Following the discussion of FIG. 1, specific details of the various embodiments of the present disclosure are described with reference to FIGS. 2-5.

Overview of Example Network Environment

FIG. 1 illustrates one embodiment of a system for administering medication via an infusion pump in a network environment 100. The medication management system (MMS) shown in FIG. 1 includes a medication management unit (MMU) server 3108 and a medical device, such as infusion pump 3130, operating in conjunction with one or more information systems or components of a hospital environment.

Intravenous (IV) fluid(s) and/or medication(s) 3100 in containers 3102 may be administered to a patient 3104 using the system shown in FIG. 1. Although the system shown in FIG. 1 utilizes barcodes and a barcode reader as apparatus to input and read machine-readable information, those skilled in the art will appreciate that other apparatus for reading or inputting information may be utilized. Moreover, a point of care (POC) client 3126 may include an identification receiver 32 adapted to recognize such indicia may be provided in the MMS.

In certain aspects, the IV fluids and/or medications 3100 in container 3102 may be provided with new or supplemental labels with a unique infusion order identifying barcode by a pharmacist according to certain hospital practices. Specifically, drug container specific identification information, such as barcoded information on the container 3102 may include patient identification information, medication identification information, universal identification information, medical device delivery information, and/or medication order information. The IV fluids and/or medications 3100 in barcode-identified containers 3102 may be supplied to hospitals by various vendors, with preexisting unique barcode identifiers, which include medication information and other information, such as a National Disease Center (NDC) code, expiration information, drug interaction information, and the like.

In some aspects of the disclosure, the universal identification information on the container 3102 may be a unique medication order identifier that, by itself, identifies the order associated with the container. In other aspects, the identification information on the container 3102 may be a composite patient/order code that contains both a patient ID (such as a medical record number) and an order ID unique only within the context of the patient. In certain aspects, the identification information on the container 3102 may include a medication ID. The system identified in FIG. 1 may include a drug library editor (DLE) client 3106, such as a notebook, desktop or server computer. The DLE client 3106 may include DLE software. As described above, the MMU server 3108 may have MMU software that is installed and runs on the MMU server 3108. The drug library and other databases may be stored on the MMU server 3108, on a separate server, and/or in remote locations.

Hospital information systems (HIS) 3110 may include one or more computers connected by cabling, interfaces, and/or Ethernet connections. Alternatively, wireless connections and communications may be used in whole or in part. Servers provide processing capability and memory for storage of data and various application programs or modules, including but not limited to an admissions-discharge-and-transfer (ADT) module or computer 3112, a computerized physician order entry (CPOE) module or computer 3114, and a pharmacy information system (PIS) module or computer 3116. Hospital personnel, such as admission clerks 3118, physicians 3120, and pharmacists 3122, respectively, may be authorized to access these modules through client workstations connected to the servers in order to enter data, access information, run reports, and complete other tasks.

In the embodiment shown in FIG. 1, the HIS 3110 may also include a POC system 3125 including a server or POC computer 3124 (sometimes referred to as a barcode point of care server or computer), or the POC computer 3124 may be separate from the HIS 3110. The POC computer 3124 may act as a part of the POC system 3125 (sometimes referred to as the barcode point of care system or BPOC) and may be able to wirelessly communicate through a plurality of wireless communication nodes located throughout the hospital, utilizing a wireless communications protocol, such as IEEE 801.11, IEEE 802.11, or Bluetooth. The POC computer 3124 may communicate wirelessly with a portable thick client, POC client 3126, carried by a caregiver. The POC client 3126 may be a personal digital assistant (PDA) that includes significant memory, display, and processing capabilities. The POC client device may execute a variety of programs stored in its memory in some degree independently of the POC computer 3124.

In one embodiment of FIG. 1, the MMU server 3108 may be hard-wired to the DLE client 3106 and to a MMU client 3128. Alternatively, the MMU and DLE client functions may be combined onto a single client computer/workstation or may reside together with the MMU server 3108 on a single combined MMU/DLE server. The MMU server 3108 may reside in a location remote from the patient's room or treatment area. For instance, the MMU server 3108 may reside in a secure, climate controlled information technology room with other hospital servers, and computer equipment and its client terminals may be located in the pharmacy, biomedical engineering area, nurse station, or ward monitoring area. One MMU server 3108 may monitor, coordinate, and communicate with many infusion pumps 3130. For example, in one embodiment, the MMU software running on the MMU server 3108 may support up to one thousand infusion pumps concurrently.

In embodiment of FIG. 1, the POC client 3126 in the POC system 3125 may communicate through the POC server 3124 with the MMU server 3108. The MMU server 3108 may interface or communicate wirelessly with the infusion pump 3130 through the same wireless nodes utilized by the POC system 3125 and a connectivity engine and antenna on or in the infusion pump 3130. Communication between the infusion pump 3130 and the POC client 3126 may take place through the MMU server 3108 and POC server 3124. The MMU server 3108 may store in an associated memory both the logical ID and the network ID or Internet Protocol (IP) address of the infusion pump(s) 3130, such that only the MMU server 3108 may communicate in a direct wireless manner with the infusion pump 3130. Alternatively, the MMU server 3108 may provide the IP address and other information about the infusion pump 3130 to the POC system 3125 to facilitate direct communication between the POC system 3125 and the infusion pump 3130.

Upon admission to the hospital, the admission clerk 3118 or similar personnel may enter demographic information about each patient 3104 into an associated memory of the ADT module or computer 3112 of an HIS database stored in an associated memory of the HIS 3110. Each patient 3104 may be issued a patient identification wristband, bracelet, or tag 112 that may include an identifier 3103, such as a barcode or RFID tag, identifying the patient. The wristband, bracelet, or tag 112 may also include other information, in machine readable or human-readable form, such as the name of the patient's doctor, blood type, allergies, and the like.

The patient's doctor 3120 may prescribe medical treatment by entering a medication order into the CPOE module or computer 3114 within the HIS 3110. The medication order may specify a start time, stop time, a range of allowable doses, physiological targets, route, and site of administration. In the case of an order for infusion of fluids or medication, the order may be written in various formats, and may include the patient's name, patient ID number, a unique medication order or prescription number, a medication name, medication concentration, a dose or dosage, frequency, and/or a time of desired delivery. This information may be entered into the memory of the CPOE module or computer 3114, and may be stored in a memory associated with at least the POC server 3124.

The medication order may also be delivered electronically to the PIS module or computer 3116 in the pharmacy and may be stored in an associated memory. The pharmacist 3122 may screen the prescribed order, translate it into an order for dispensing medication, and prepare the medication or fluids with the proper additives and/or necessary diluents. The pharmacist 3122 may prepare and affix a label 102 with drug container specific identifying information 3101 to the medication or drug container 3102. The label may include in machine-readable and/or human-readable form medical device specific delivery information including but not limited to the dispense ID number, patient ID, drug name, drug concentration, container volume, volume-to-be-infused ("VTBI"), rate, duration, and the like. Only two of the three variables VTBI, rate, and duration may be defined as the third may be calculated when the other two are known. The labeled medication may be delivered to a secure, designated staging location or mobile drug cart on the ward or floor near the patient's room or treatment area. The medication order pending dispensing or administration may be posted to a task list in the HIS 3110 and POC system 3125 and stored in an associated memory.

The caregiver 3132 (e.g., a nurse) may use the identification receiver 32 associated with the POC client 3126 to scan his/her caregiver identification badge 116 and enter a password, which logs the caregiver into the system and authorizes the caregiver to access a nurse's task list from the POC system 3125 through the POC client 3126. The caregiver 3132 may view from the task list that IV drugs are to be administered to certain patients 3104 in certain rooms. The caregiver 3132 obtains the necessary supplies, including medications, from the pharmacy and/or a staging area in the vicinity of the patient's room.

The caregiver 3132 may take the supplies to a patient's bedside, turn on the infusion pump 3130, verify that the network connection icon on the infusion pump 3130 indicates a network connection (for example, a wireless connection such as Wi-Fi or the like) is present, select the appropriate clinical care area (CCA) on the infusion pump 3130, and mount the IV bag, container, or vial 3102 and any associated tube set as required in position relative to the patient 3104 and infusion pump 3130 for infusion. Another connection icon on the infusion pump 3130 or pump user interface screen can indicate that a wired or wireless connection to the MMU server 3108 is present. Using the identification receiver/reader integral to the POC client 3126, the caregiver 3132 may scan the barcode on the patient's identification wristband, bracelet, or tag 112 or other patient identification device. A task list associated with that particular patient may appear on the POC client 3126 screen. The task list, which may also include orders to give other forms of treatment or medication by other routes (oral, topical, etc.), may be obtained from the HIS 3110 via the POC server 3124 and communicated wirelessly to the POC client 3126. In one embodiment, the list is generated by matching the scanned patient ID with the patient ID for orders in memory within the POC server 3124. In another embodiment, the order information may be obtained by scanning the drug container specific identification information for associated orders in memory within the POC server 3124, through the following step(s).

The caregiver 3132 may scan the medication barcode label 102 containing medication container specific identification information 3101 on the medication container 3102 with the POC client 3126. The POC client 3126 may highlight the IV administration task on the task list and send the scanned medication container specific identification information, such as dispense ID information, from the medication container 3102, to the POC server 3124. The POC server may use the medication container specific identification information to pull together the rest of the order details and send them back to the POC client 3126. The POC client 3126 may then display an IV Documentation Form on its screen. One side of the IV Documentation Form screen may show the order details as "ordered" and the other side may be reserved for a status report from the infusion pump 3130. The status report from the infusion pump 3130 may be transmitted to the POC client 3126 through the POC server 3124 and MMU server 3108. The lower portion of the IV Documentation Form screen may provide the caregiver 3132 with instructions (like to scan the infusion pump 3130 barcode) or identify whether the pump is running or stopped.

The caregiver 3132 may then scan the barcode label 92 associated with the infusion pump 3130 (or pump channel if the pump is a multi-channel pump). The barcode label 92 may contain medical device specific identification information 3131, such as the logical name and/or logical address of the device or channel. The POC system 3125 then automatically bundles the information into a program pump request containing the "order details" and in one embodiment, without further interaction with the caregiver 3132, transmits this information to the MMU server 3108.

The program pump request may include at least some of the following information (in HIS/POC system format): a Transaction ID, which may include a Logical Pump ID, a Pump Compartment, a Pump Channel ID, a Reference Device Address, a Caregiver ID, a Caregiver Name, a Patient/Person ID (HIS identifier), a Patient Name, a Patient Birth Date & Time, a Patient Gender, a Patient Weight, a Patient Height, and an Encounter ID which may include a Room, a Bed, and a Building (including CCA). The program pump request may also include Order Information or "order details", including an Order ID, a Start Date/Time, a Stop Date/Time, a Route of Administration, a Rate, a Duration of Infusion (Infuse Over), a Total Volume to be Infused (VTBI), an Ad Hoc Order Indicator, and Ingredients including HIS Drug Name or HIS Generic Drug Name, HIS Drug Identifier or HIS Generic Drug ID, Rx Type (Additive or Base), Strength w/units, and Volume w/units. The program pump request may further include Patient Controlled Analgesia (PCA) Orders Only information, such a PCA Mode-PCA only, Continuous only, or PCA and Continuous, a Lockout Interval (in minutes), a PCA Continuous Rate, a PCA Dose, a Loading Dose, a Dose Limit, a Dose Limit Time w/units, a Total Volume in vial or syringe, and Order Comments.

The MMU server 3108 may map or convert the wide range of expressions of units allowed by the HIS 3110 or POC system 3125 for POC client 3126 requests into the much more limited set of units allowed in the MMU server 3108 and infusion pump 3130. For example, the POC client 3126 request may express "g, gm, gram, or grams" whereas the MMU server 3108 and/or infusion pump 3130 may accept "grams" only. Infusion pump 3130 delivery parameters or infusion pump 3130 settings are mapped or converted from corresponding order information or "order details" of the program pump request.

The MMU server 3108 may store in an associated memory a mapping or translation table that keep track of the logical ID, serial number or other identifier of an infusion pump 3130 and the corresponding current network (static or dynamic) address (Internet Protocol (IP) address) or ID of the infusion pump 3130 on the network, which in this example is a wireless network. The MMU server 3108 may be able to translate or associate a given identifier of the infusion pump 3130 with its network address in the translation table and provide the network IP address to the requesting POC system 3125 or device. The MMU server 3108 may also store in an associated memory and/or look up the drug library applicable to the scanned infusion pump 3130 and/or convert the Drug ID and Strength from the pump program request into an index number of the medication at the desired strength or concentration from the drug library. The duration of the infusion may come from the POC system 3125 in hours and minutes and may be converted to just minutes for the infusion pump 3130 to recognize it. Volume or VTBI may be rounded to provide a value-specific and infuser-specific number of digits to the right of the decimal point. Units (of drug) may be converted to million units where appropriate. Patient weight may be converted and either rounded according to infuser-specific rules or not sent to the infuser.

Once the MMU server 3108 transforms the information from the program pump request into infusion pump settings or delivery parameters and other information in a format acceptable to the infusion pump 3130, the MMU server 3108 may wirelessly download a command message to the infusion pump 3130. If the infusion pump 3130 is not already equipped with the latest appropriate version of the hospital-established drug library, the MMU server 3108 may also automatically download a drug library to the infusion pump 3130. The hospital-established drug library may be maintained in a separate process undertaken by the biomedical engineer or pharmacist 3122 to place limits on the programming of the infusion pump 3130, as well as other infusion pump operating parameters such as default alarm settings for air in the line, occlusion pressure, and the like. The drug library may set up acceptable ranges or hard and/or soft limits for various drug delivery parameters in the infusion pump 3130.

The MMU server 3108 may also download to the infusion pump new versions, patches, or software updates of the infusion pump's internal operating system software. The infusion settings or delivery parameters and other information from the MMU server 3108 may be entered into the memory of the infusion pump 3130 and the infusion pump 3130 settings may automatically populate the programming screen(s) of the infusion pump 3130, just as if the caregiver 3132 had entered the information and settings manually. The infusion pump 3130 screen may populate with the name of the drug and drug concentration based on the drug library index number, patient weight, rate, VTBI, and/or duration. Further, the MMU server 3108 may transmit one or more synchronization signals or screen content display rules/parameters to the infusion pump 3130. A return message of confirmation signal may be sent to the MMU server 3108 by the infusion pump 3130 to indicate that the command message has been received. At this point, if necessary, the caregiver 3104 may manually enter any additional infusion settings or optional information that was not included in the command message.

The infusion pump 3130 may then prompt the caregiver 3132 to start the infusion pump 3130 by pressing the start button. When the caregiver 3132 presses the start button, a confirmation screen with the infusion settings programmed may be presented for confirmation and an auto-program acknowledgment message can be sent to the MMU server 3108 to forward without request (e.g., pushed in a near real-time manner) or provide to the POC system 3125 when requested or polled. When the caregiver 3132 presses the button to confirm, the infusion pump 3130 may begin delivering fluid according to the programmed settings. The infusion pump 3130 may send a status message to the MMU server 3108 indicating that the infusion pump 3130 was successfully auto-programmed, confirmed and started by the caregiver 3132, and is now delivering fluid. This information may also be displayed at the infusion pump. The MMU server 3108 may continue to receive logs and status messages wirelessly from the infusion pump 3130 periodically as the infusion progresses or when alarms occur.

The MMU server 3108 may report a portion of the initial status message to the POC client 3126 through the POC server 3124 (in MMU format) to indicate that the infusion pump 3130 has been auto-programmed and the caregiver 3132 has confirmed the settings. The MMU server 3108 may communicate to the POC system 3125 and/or at the infusion pump 3130 the actual Rate, VTBI, and Duration. A notation at the bottom of the screen of the POC client and/or the infusion pump may indicate that the infusion pump 3130 is running. The infusion pump 3130 may compare and give a visual, audio, or other type of affirmative signal if the pump information matches or acceptably corresponds with the ordered information. An initial determination of whether the pump information matches the order may be done in the MMU server 3108 and communicated to the POC client 3126 through the POC server 3124. Alternatively, the POC server 3124 or the infusion pump 3130 may make the necessary comparisons. If the pump information does not match the order, the infusion pump 3130 at the display 88 may output a visual, audio, or other type of negative signal, which may include an error message.

The caregiver 3132 may be prompted to review and press a save button on the infusion pump 3130 if the order has been begun as desired or any variations are acceptable. The MMU server 3108 may receive status, event, differences, and variation information from the infusion pump 3130 and pass such information to the POC system 3125. In a separate subsequent step, the nurse may electronically sign the record and presses a send button on the POC client POC client 3126 to send the information to the patient's electronic medication record (EMR) or medication administration record (MAR).

Other Environments

FIG. 1 illustrates one example environment in which the various display synchronization techniques of the present disclosure may be utilized. However, the embodiments described herein are not limited to such an environment, and may be applied to any networked or non-networked environment. An example infusion pump that may be used in one or more of such environments is described below with reference to FIG. 2.

Architecture of Infusion Pump

Figure 2:
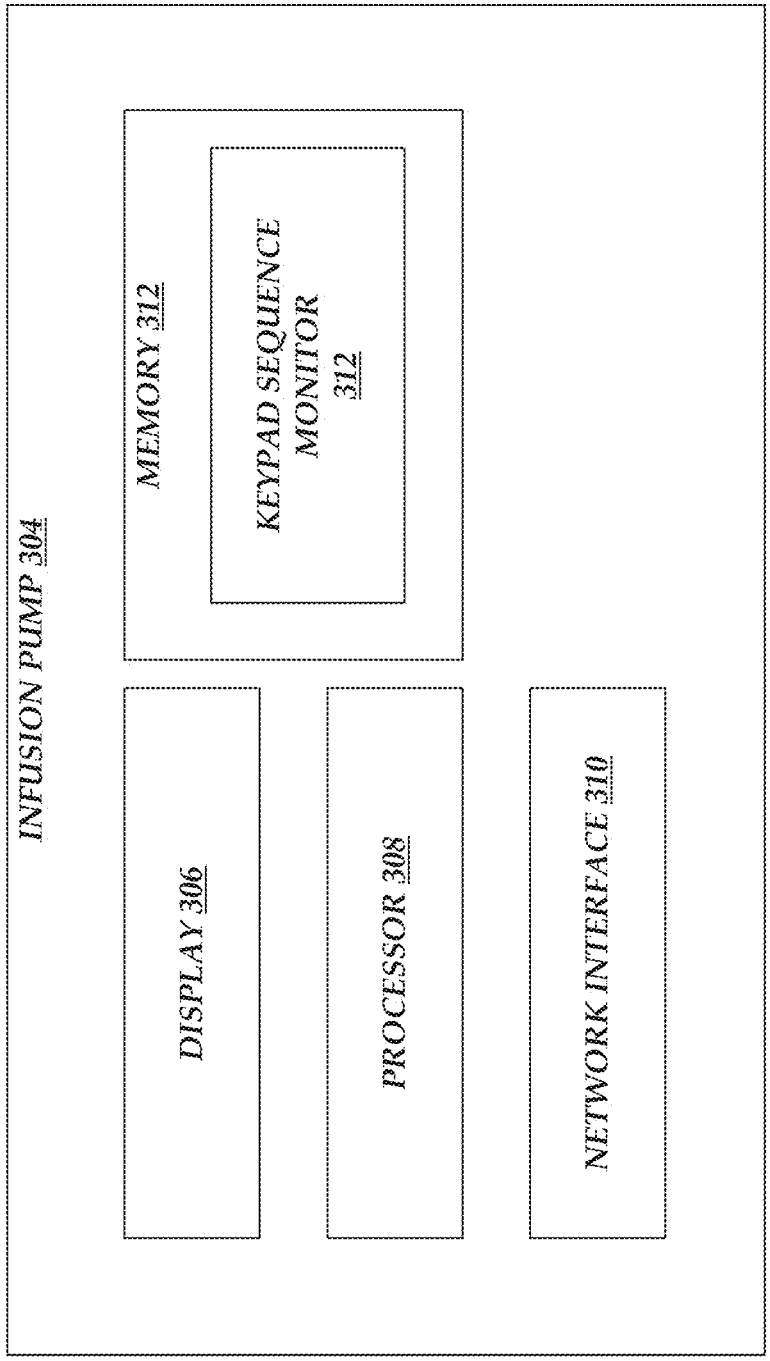
FIG. 2 is a block diagram illustrating components of an example infusion pump in accordance with aspects of the present disclosure.

With reference to FIG. 2, the components of an example infusion pump are described in greater detail. The example architecture of the infusion pump 304 depicted in FIG. 2 includes an arrangement of computer hardware and software modules that may be used to implement aspects of the present disclosure. The infusion pump 304 may include many more (or fewer) elements and/or sub-elements than those shown in FIG. 2. It is not necessary, however, that all of these elements be shown in order to provide an enabling disclosure.

As illustrated, the infusion 304 includes a display 306, a processor 308, a network interface 310, and a memory 312, all of which may communicate with one another by way of a communication bus. The display 306 may display information generated or stored by the infusion pump 304 or any other information associated with the infusion pump 304. For example, infusion pump 304 may be used to deliver medication to a patient. In such a case, the display 306 may display the volume of the medication infused so far, the volume of the medication to be infused, the rate at which the medication is being infused, and the like. Examples of such displays are illustrated in FIG. 3A through FIG. 3D. The display 306 may also provide a keypad to the user for data entry and programming.

The processor 308 may receive information and instructions from other computing systems or services via a network. The processor 308 may also transmit information to and receive information from the memory 312 and further provide content to the display 306 for display. The network interface 310 may provide connectivity to one or more networks or computing systems in the network environment described herein. For example, the network interface 310 may be a serial port, a parallel port, or any other communication interface that can enable or facilitate wired or wireless communication according to any communication protocols such as Zigbee (e.g., IEEE 802.15.4), Bluetooth, Wi-Fi (e.g., IEEE 802.11), Near Field Communication (NFC), and the like.

The memory 312 may contain computer program instructions (grouped as modules in some embodiments) that the processor 308 can execute in order to implement one or more aspects of the present disclosure. The memory 312 may include RAM, ROM, and/or other persistent, auxiliary, or non-transitory computer-readable media. In some embodiments, the memory 312 stores an operating system that provides computer program instructions for use by the processor 308 in the general administration and operation of the infusion pump 304. As illustrated in FIG. 2, the memory 312 may include a keypad sequence monitor 312. In some embodiments, the keypad sequence monitor 312 implements various aspects of the present disclosure.

Although not shown in FIG. 2, the infusion pump 304 may further include one or more input devices such as a touch screen, mechanical buttons, or a voice recognition system. Further, the infusion pump 304 may include one or more additional storage devices for storing data generated by the infusion pump 304 or other data utilized in implementing aspects of the present disclosure.

Infusion Pump Displaying Context Cues Determined from User Keypresses

With reference now to FIGS. 3A-3D, example infusion pump displays illustrating keypress analysis on a keypress-by-keypress basis will be described. FIGS. 3A-3D illustrate embodiments of an infusion pump display 306. The display 306 includes various context parameters 502, 504, a graphical limit indicator 508, data entry fields 510, 512, 514, 516, a keypad 518, and various action buttons 520, 522. The context parameters include a drug selection field 502 and a clinical care area ("CCA") selection field 504. The graphical limit indicator 508 indicates lower and upper hard limits (0 mcg/kg/min and 50 mcg/kg/min in the illustrated example) as well as lower and upper soft limits (2.5 mcg/kg/min and 20 mcg/kg/min in the illustrated example). The data entry (or treatment parameter) fields include a patient weight entry field 506, a drug dosing field 510, an infusion rate field 512, a volume-to-be-infused field 514, and an infusion duration field 516. The graphical limit indicator 508 may appear beneath a particular data entry field once the data entry field is selected. The numbers on the graphical limit indicator 508 will vary depending upon the selected context parameters and the selected data entry field. The keypad 518 includes various numerical keys 524 (digits 1-9 and a decimal point key), a backspace key 526 and an ENTER key 528. The numerical keys 524 are used by the user to input values into each of the data entry fields. The action buttons include a CANCEL key 520 and a CONFIRM key 522. The CANCEL key 520 may be used by the user to cancel all entries made, but not yet confirmed. The CONFIRM key 522 may be used by the user to confirm that all values entered are to be submitted to the infusion pump's microprocessor for further processing and to execute an infusion program according to the settings and values shown on the pump's display 306.

Figure 3A:
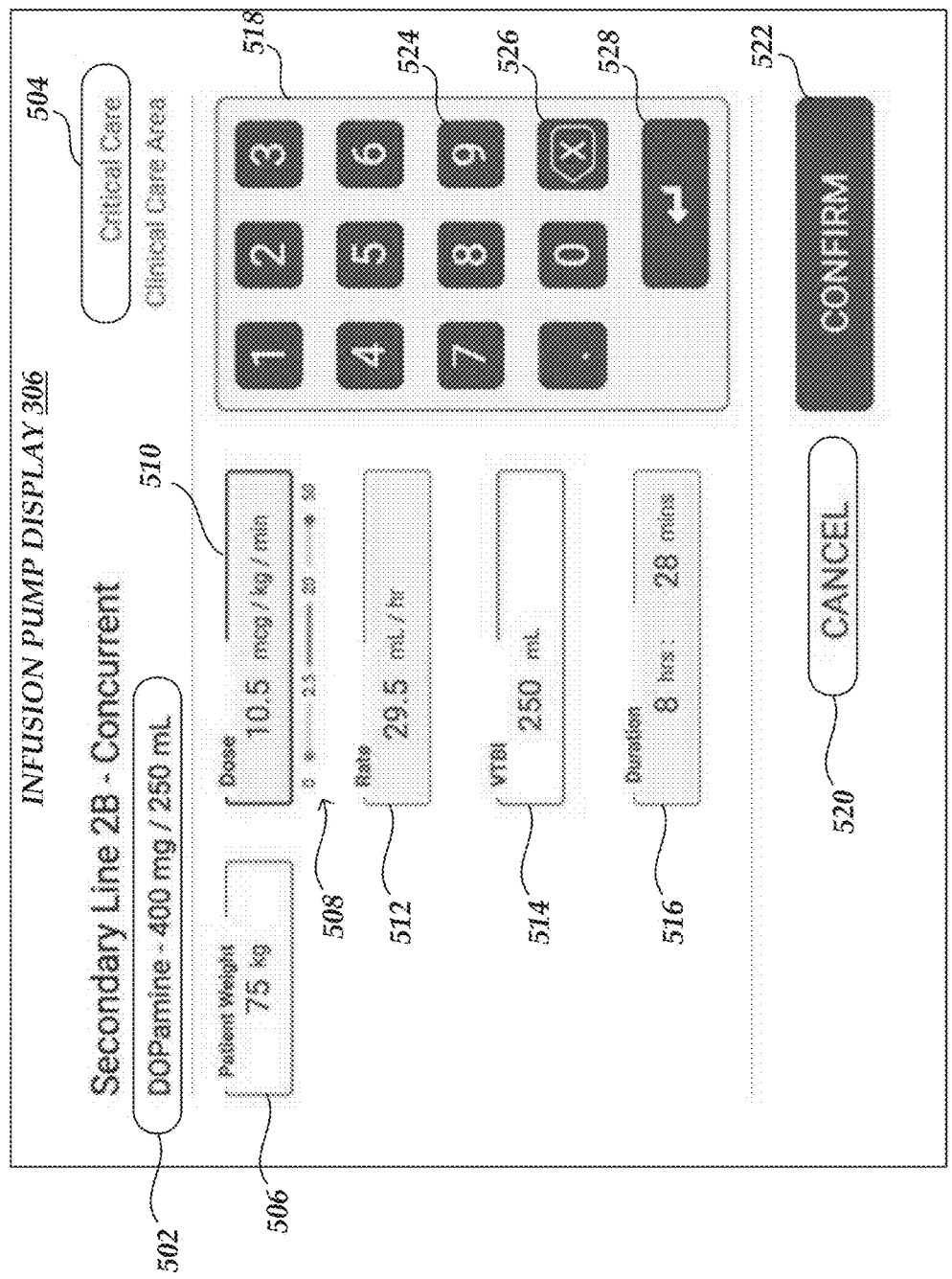
FIGS. 3A-3D illustrate example display screens of the infusion pump of FIG. 2 showing one implementation of a safety sequence keypad.

In the display 306 of FIG. 3A, the user has selected the drug DOPamine at a concentration of 400 mg/250 mL for infusion to the medical patient using the drug selection field. In one embodiment, when the drug selection field 502 is selected, a list of drugs at particular concentrations are presented in a drop-down menu. In the illustrated embodiment, the drug selection field 502 presents the user with the option to select drug and drug concentration via the same field (e.g., the dropdown menu may present "DOPamine—400 mg/250 mL" as one selectable value, and "DOPamine—200 mg/250 mL" as a second selectable value). In other embodiments (not illustrated) drug and drug concentration are independently selectable by the user via two distinct fields, such as a drug selection field 502 and a drug concentration selection field (not shown). For example, the drug "DOPamine" may be one of several drugs selectable by the user via the drug selection field 502, and the concentration "400 mg/250 mL" may be one of several drug concentrations selectable by the user via a drug concentration selection field (not shown). The methods described herein are applicable to both embodiments and references to using the drug selection as a context parameter 502 refers to using both a drug selection and drug concentration selection as context parameters. The user has also used the CCA selection field 504 to select the "Critical Care" CCA. Using one or more of these context parameters 502, 504 the infusion pump accesses a drug library and determines lower and upper soft and hard limits to be used by the pump to restrict further data entry and programming by the user. Since the user has selected the dose field 510 for setting the infusion therapy dose value, the lower and upper soft and hard limits are graphically displayed on a graphical limit indicator 508 positioned beneath the dose field 510. The graphical limit indicator 508 indicates that for the selected context parameters 502, 504, the lower and upper soft limits for the dosing parameter are 2.5 and 20 mcg/kg/min and the lower and upper hard limits for the dosing parameter are 0 and 50 mcg/kg/min, respectively. In the display 306 of FIG. 3A, the user has entered the value 10.5 mcg/kg/min, which between the lower and upper soft limits, and therefore a valid value that may be entered without restriction. In the illustrated embodiment, the user has also entered the patient's weight (in kilograms) in the patient weight field 506. The patient's weight is used as a treatment parameter in connection with the dose value (which may be entered in terms of mcg/kg/min or micrograms of drug per kilogram of patient weight per minute). In some embodiments, the dose value is entered in terms of mcg/min, or micrograms of drug per minute, independent of the patient's weight.

Figure 3B:
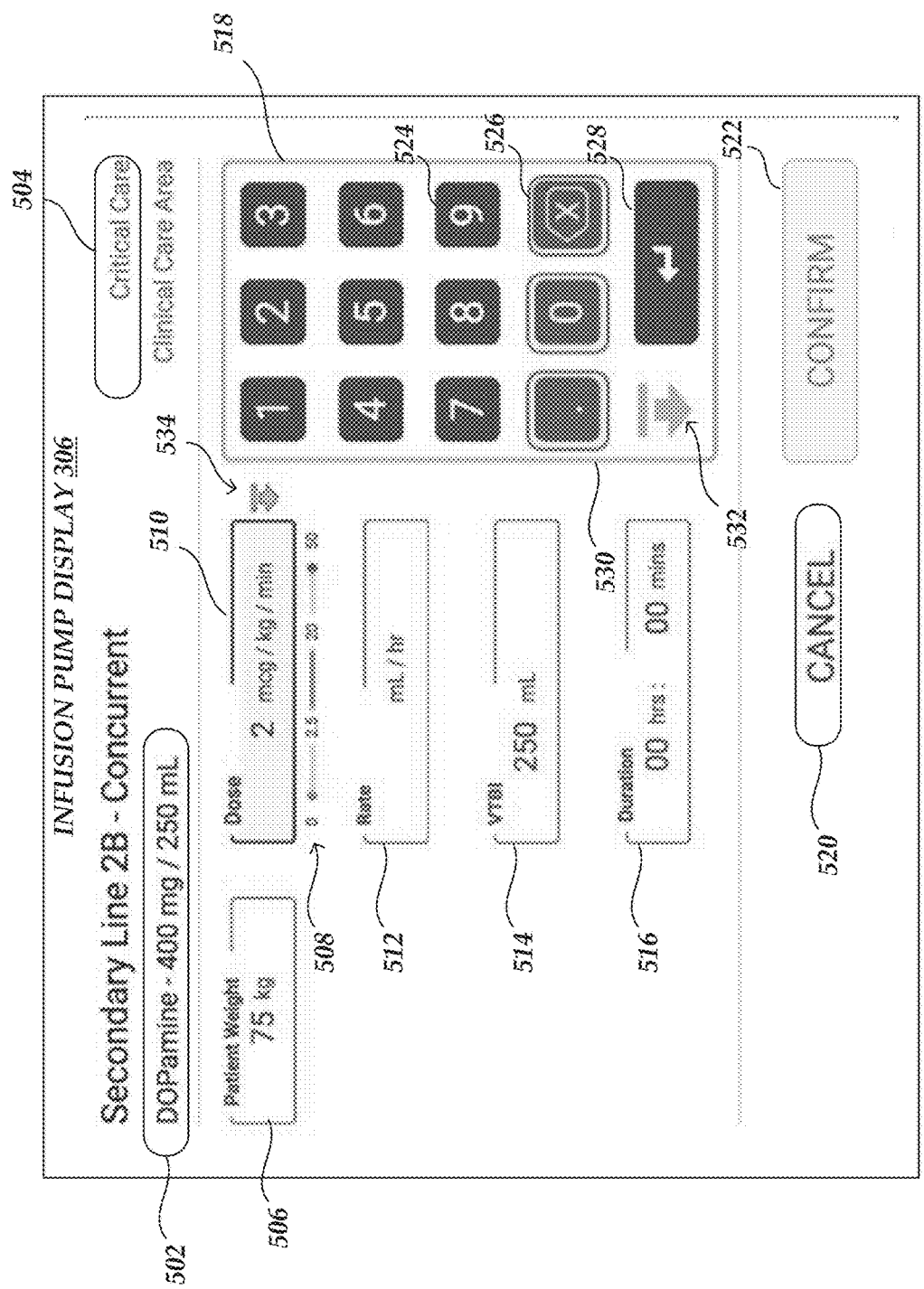
Figure 3C:
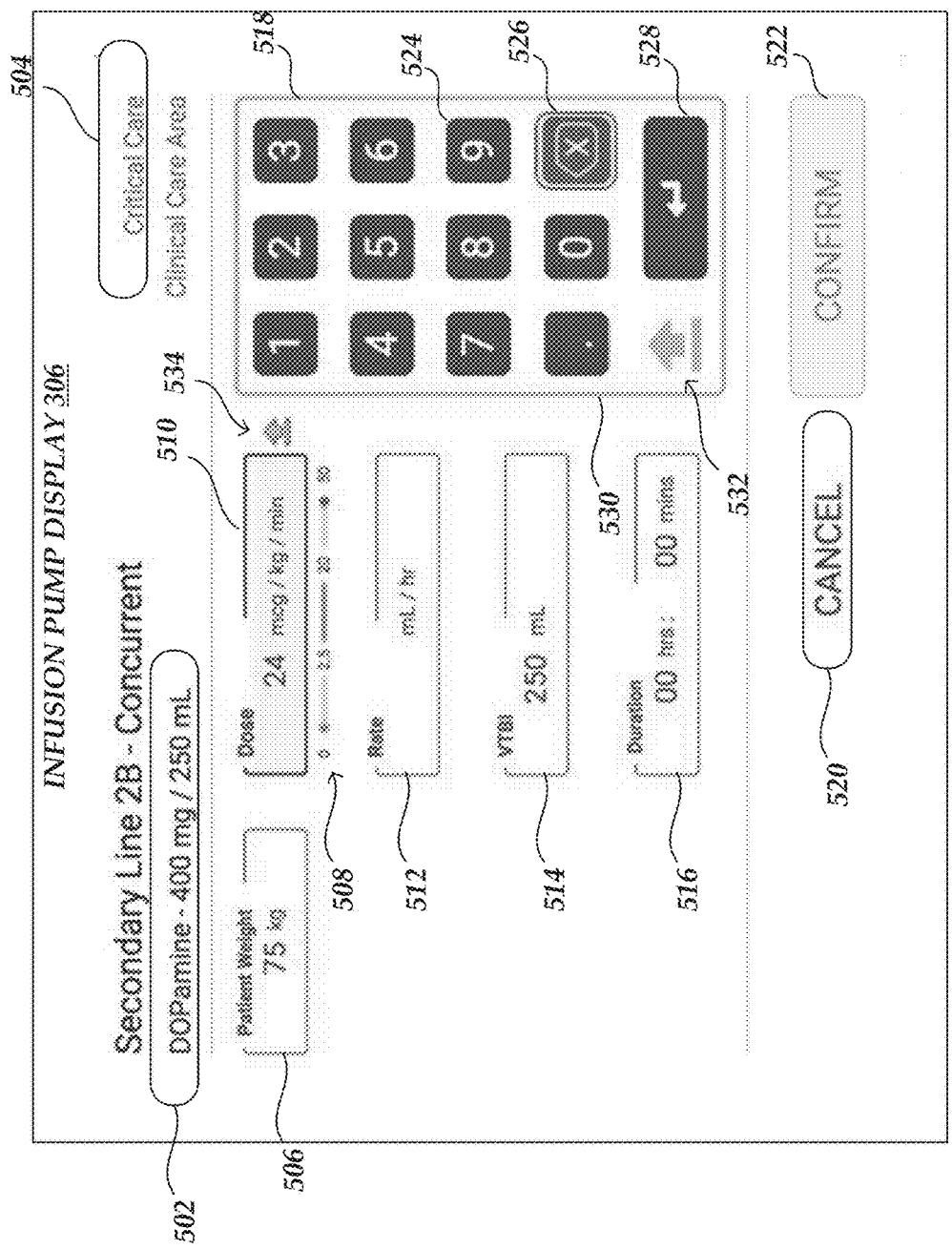
Figure 3D:
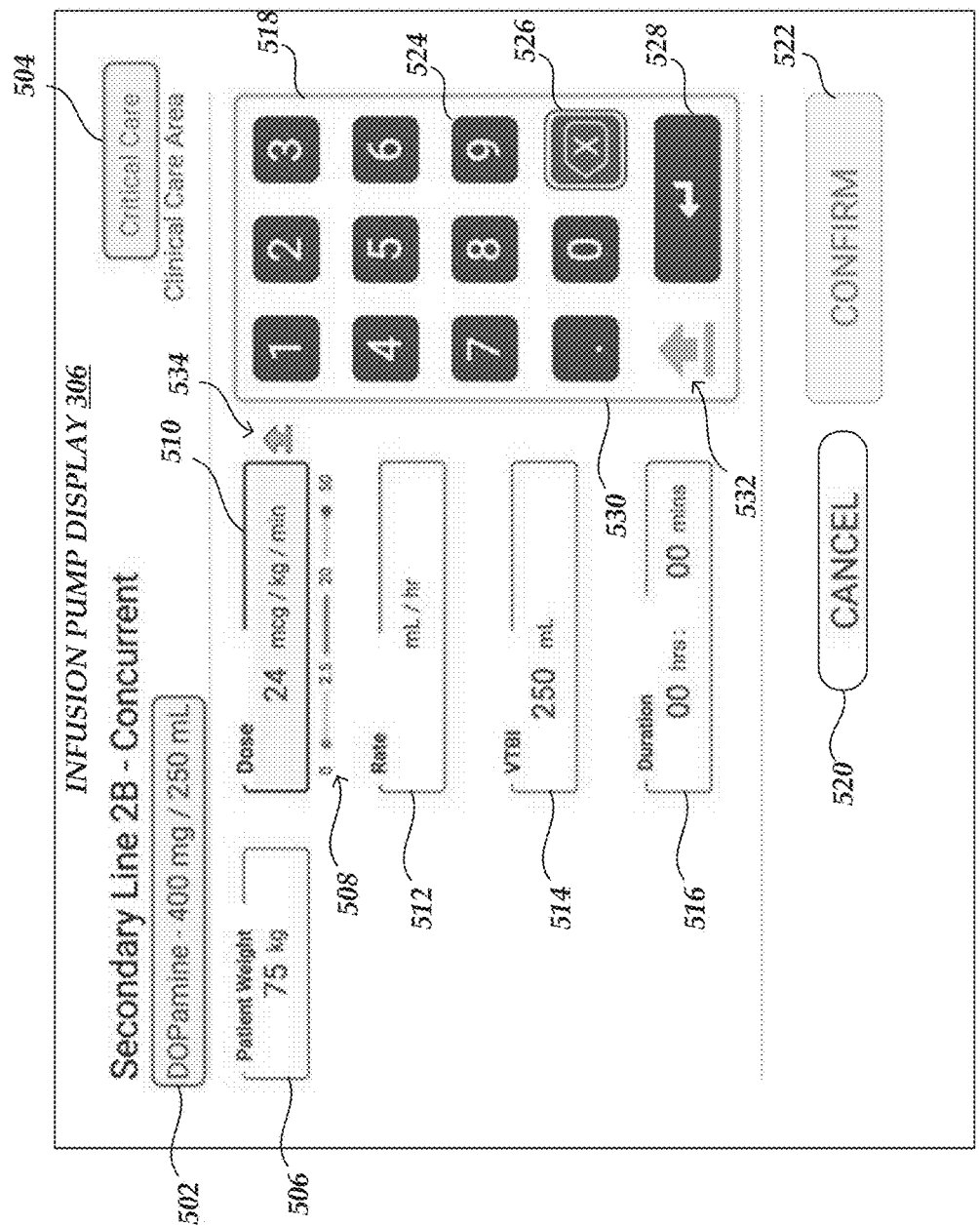

FIG. 3B-D illustrates a display 306 of an infusion pump where each keypress is analyzed and context cues and other indicators are activated to guide a user to enter a valid treatment parameter value. For example, a keypad sequence monitor (such as the keypad sequence monitor 312 of FIG. 2) may analyze each keypress and provide guiding indicators to the user to guide the user to enter a valid value. As in FIG. 3A, the user has selected the drug DOPamine at a concentration of 400 mg/250 mL for infusion to the medical patient using the drug selection field. In one embodiment, when the drug selection field 502 is selected, a list of drugs at particular concentrations are presented in a drop-down menu. As discussed above, both the drug selection and the drug concentration selection are both context parameters, whether selected simultaneously via a single drop down menu, or whether they are independently selected via separate drop down menus. The user has also used the CCA selection field 504 to select the "Critical Care" CCA. Using one or more of these context parameters 502, 504, the infusion pump accesses a drug library and determines lower and upper soft and hard limits to be used by the pump to restrict further data entry and programming by the user. Since the user has selected the dose field 510 for setting the infusion therapy dose value, the lower and upper soft and hard limits are graphically displayed on a graphical limit indicator 508 positioned beneath the dose field 510. The graphical limit indicator 508 indicates that for the selected context parameters 502, 504, the lower and upper soft limits for the dosing parameter are 2.5 and 20 mcg/kg/min and the lower and upper hard limits for the dosing parameter are 0 and 50 mcg/kg/min, respectively.

The after selecting the dose field 510 for data entry, the user has entered the value of 2 using a numerical key of the display 306 keypad 518. The display 306 responds by providing warnings to the user that the value of 2 is an invalid value, as it is between the lower hard limit and lower soft limit values defined by the drug library, as illustrated on the graphical limit indicator 508. However, because the value of 2 is below only the lower soft limit (and not below the lower hard limit), the soft limit restriction may be overridden by the user. The display 306 provides a warning indicator 530 to indicate that the value entered so far ("2" in this example) is invalid, but may be overridden. The warning indicator 530 includes a colorful outline around the keypad 518. In some embodiments, the warning indicator 530 can include a flashing area, such as a flashing key, or outline, and/or background portion of the display 306. An audible indicator may be provided in addition to or instead of the visual warning indicator 530.

The display 306 also now includes a lower limit override key 532, which may be selected by the user to override the lower soft limit defined by the drug library. In addition, a limit value warning indicator 534 is provided next to the field (the dose field 510, in this example) in which the invalid value (the value "2" in this example) has been entered. The limit value warning indicator 534 is presented as a downward pointing arrow to indicate that the entered sequence value is below the lower soft limit value, but greater than the lower hard limit value. The sequence value refers to a value associated with the sequence of numerical keys that have been pressed at a particular point in time. The sequence value will typically change after each numerical keypress on the keypad (including pressing the decimal point or BACKSPACE keys). For example, if the user initially presses the key "2," the sequence value will be initially set to a value of 2. If the user next presses the key "4," the sequence value will change to the value 24. If the user next presses the BACKSPACE key, the sequence value will change back to the value of 2.

In addition, the keypad sequence monitor determines that a subsequent keypress by the user could result in a valid treatment parameter value entry (e.g., a value between 2.5 and 20 mcg/kg/min, as defined by the drug library in this example). In the illustrated example, the user has entered the value 2 so far. Therefore, a subsequent keypress of the decimal point or the key zero (or the BACKSPACE key to delete the value 2), could result in a valid treatment parameter value entry. Any other numerical keypress would result in an invalid value (e.g., 21-29). Therefore, the decimal, "0" and BACKSPACE keys are further enhanced to include additional indicators to indicate to the user that the user may wish to consider pressing one of these keys if the user wishes to enter a valid dose parameter value. In the embodiment of FIG. 3B, the addition indicator includes an enhanced border and key background color that is different than the other numerical keys 524 of the keypad 518. Any other additional indicator may be provided in addition to, or instead of, the additional indicators of FIG. 3B.

The user next presses the key "4" on the keypad 518, as shown in FIG. 3C. Therefore, the sequence entered so far is "2" and "4", which corresponds to a sequence value of 24. The sequence value is displayed in the dose field 510. In addition, the keypad sequence monitor determines that the sequence value is invalid because it violates (e.g., exceeds) the upper soft limit restriction, which is 20 mcg/kg/min in this example. However, because the sequence value does not violate the upper hard limit restriction (of 50 mcg/kg/min), the upper soft limit restriction may be overridden by pressing the limit override key 532. The limit override key 532 has changed to an upward pointing arrow to indicate that the entered sequence value is greater than the upper soft limit value. In addition, the limit value warning indicator 534 is presented as an upward pointing arrow to indicate that the entered sequence value is above the upper soft limit value, but less than the upper hard limit value.

In addition, indicators presented with the keys 524, 526 of the keypad 518 are further updated in response to the current sequence value ("24" in this example). Indicators are removed from all numerical keys because any subsequent numerical keypress would result in an invalid sequence value (e.g., 240-249). Indeed, the only subsequent keypress that could result in a valid sequence value is the BACKSPACE or DELETE key 526, which is highlighted. The indicator (e.g., highlighting, distinct color background, etc.) presented with the BACKSPACE key 526 indicates to the user that this is the only key that could result in a valid sequence value.

Figure 4A:
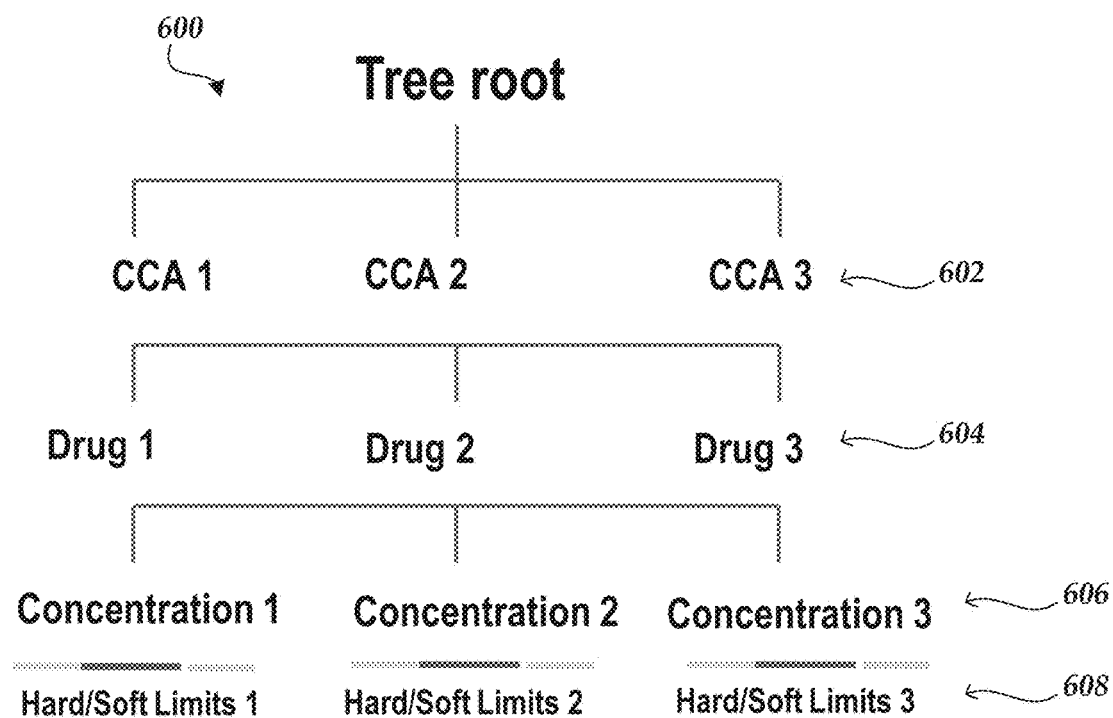
FIGS. 4A-4B illustrate example parameter limit tree structures showing examples of context parameters that may be used by the safety sequence keypad of FIGS. 3A-3D.

Furthermore, the keypad sequence monitor determines that even though the currently entered sequence value ("24") is an invalid dose value, the keypad sequence monitor analyzes one or more context parameters to determine whether changing the context parameter could result in the entered sequence value ("24") as being within a valid range. For example, as illustrated in FIG. 4A, the keypad sequence monitor can utilize a parameter limit tree 600 to determine whether a different context parameter would result in the selection of soft and hard limits that define a valid range within which the entered sequence value would fall. In one embodiment, the parameter limit tree 600 is part of a drug library.

The parameter limit tree 600 of FIG. 4A illustrates a generic architecture of one embodiment of a parameter limit tree. The parameter limit tree 600 includes multiple layers 602, 604, 606, and 608, although a different number of layers may be used. Each layer 602, 604, 606 may correspond to a different context parameter (e.g., clinical care area, drug, drug concentration, etc.). The bottom layer 608 may correspond to the soft and hard limit definitions for a particular combination of context parameters 602, 604, 606. The first layer 602 of the parameter limit tree 600 corresponds to different clinical care areas ("CCA"s) within the hospital. The second layer 604 corresponds to different drugs for delivery to the patient using the infusion pump. The third layer 606 corresponds to different drug concentrations. The bottom layer 608 corresponds to the lower and upper soft and hard limit definitions for a particular drug having a particular concentration when administered in a particular CCA.

Figure 4B:
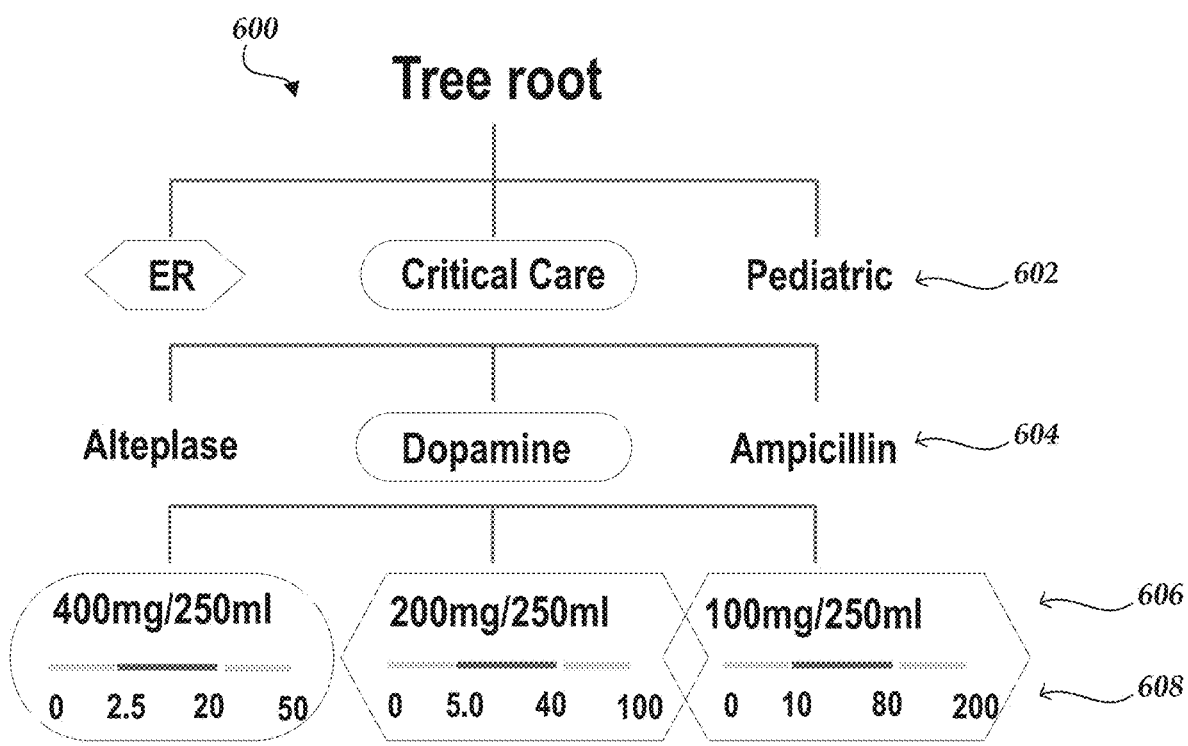

For example, as indicated in the parameter limit tree 600 of FIG. 4B, the currently selected context parameters are CCA=Critical Care, Drug=Dopamine, and Concentration=400 mg/250 ml. These context parameters correspond to lower and upper soft and hard limit values as discussed above with respect to FIGS. 3A-3D (2.5 and 20 soft limits and 0 and 50 hard limits). However, in one embodiment, by analyzing the parameter limit tree 600, the keypad sequence monitor can determine that a different Concentration context parameter selection would result in a soft and hard limit definition that would define a valid range of parameter values into which the currently entered sequence value would fall. For example, if the context parameter for drug concentration were changed from 400 mg/250 ml to 200 mg/250 ml, the lower and upper soft limit values would change from 2.5 and 20 to 5.0 and 40. Since the currently-entered sequence value (24 in this example) would be within the new valid range defined by the new soft limit values (e.g., since 24 is within the range of 5.0 to 40), the keypad sequence monitor provides an indication to the user that changing this context parameter could result in the user's entered sequence value becoming a valid value. The keypad sequence monitor may also determine that changing the drug concentration to 100 mg/250 ml, or the CCA to ER would also result in the currently-entered sequence value becoming a valid value.

Therefore, referring now to FIG. 3D, the keypad sequence monitor can provide one or more context cues, or indicators, associated with one or more context parameters. For example, the keypad sequence monitor may highlight or otherwise indicate that a change to the drug concentration context parameter 502 or the clinical care area context parameter 504 may result in the currently-entered sequence value ("24" in this example) as becoming in range. One embodiment of such context cue shown as highlighted fields with different colored backgrounds, is illustrated in FIG. 3D. In this way, the user is not only warned that a data entry value is incorrect, but also highlights the particular context parameters that have led to the determination that the value is incorrect. The user is therefore provided an indication that changing one or more of such context parameter value would re-define the acceptable range of values such that the entered value would fall within the re-defined valid range, and provides the user an opportunity to adjust such context parameter value before submitting the value (e.g., via pressing the ENTER or CONFIRM key, or equivalent), to the infusion pump for further processing.

Method of Displaying Context Cues Determined from User Keypresses

Figure 5:
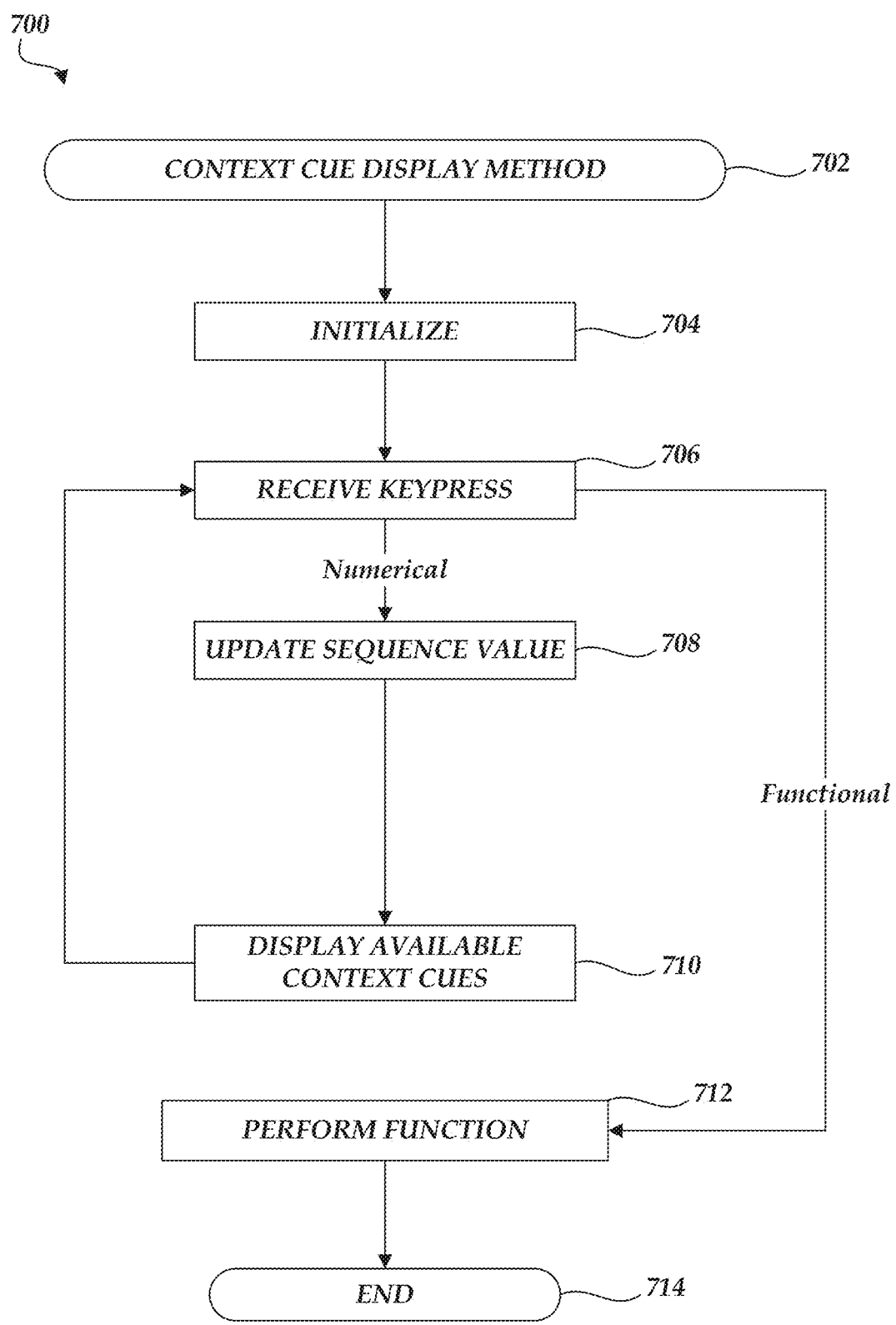
FIG. 5 illustrates an example context cue display method in accordance with aspects of this disclosure.

With reference now to FIG. 5, an example context cue display method 700 will be described. The example method 700 may be performed, for example, by the infusion pump 304 of FIGS. 2-3D (or one or more components thereof, such as the keypad sequence monitor 312). The method 700 illustrates an example algorithm that may be programmed, using any suitable programming environment or language, to create machine code capable of execution by a CPU or microcontroller of the infusion pump 304. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the infusion pump 304 that is coupled to the CPU or microcontroller and then then executed by the CPU or microcontroller. For convenience, the steps of the example method 700 are described as being performed by the keypad sequence monitor 312 of infusion pump 304.

The method 700 begins at block 702. At block 704 the keypad sequence monitor 312 initializes memory and variables based upon selected context parameters. For example, the keypad sequence monitor 312 may select and access a particular drug library, or drug library portion, based upon selected context parameters. Such context parameters may include a selected clinical care area, drug for infusion, and drug concentration. Additional or alternative context parameters may be selected, as well. Context parameters may be selected by a user via a display and keypad, including, but not limited to, any of the displays and keypads of FIGS. 3A-3D.

Using the drug library and context parameters, the keypad sequence monitor 312 may determine lower and upper soft and hard limits to be used by the keypad sequence monitor 312. Such limits will be used by the keypad sequence monitor 312 to determine whether a sequence value entered by the user for a particular treatment parameter are within a valid range, and if not, whether relevant limits may be overridden, and whether any context cues are available for display, as discussed below.

At block 706 the keypad sequence monitor 312 receives an initial keypress from the user. The keypress may correspond to a numerical value, such as any of the numerical values displayed on the keypad (e.g., 0-9, decimal point, and BACKSPACE or DELETE) or a functional key. Functional keys include context parameter selectors, fields into which data is to be entered by the user, and CANCEL or CONFIRM keys, as well as any other functional keys, including any functional keys described herein. One embodiment of such functional keys are illustrated above with respect to FIGS. 3A-3D.

If the keypress received by the keypad sequence monitor 312 is a numerical key, the method 700 proceeds to block 708, in which the entered sequence value is updated. For example, the sequence value is initially initialized to be blank. If the initially presses the key "2," the keypad sequence monitor 312 updates the sequence value to be equal to the number 2. If the user subsequently presses the key "4," the keypad sequence monitor 312 updates the sequence value to be equal to the number 24. The method 700 proceeds to block 710.

At block 710, the method 700 determines whether there are any available context cues to display. For example, if the sequence value falls outside of the valid range of values defined by the drug library (e.g., outside of the range of values between the lower and upper soft limit values), the keypad sequence monitor 312 may determine if there exists a context parameter that defines a valid range of treatment parameter values that would include the sequence value. The keypad sequence monitor 312 may use a parameter limit tree, such as the parameter limit tree 600 of FIGS. 4A-4B. Any other parameter tree, or any other method of determining whether such context parameter exists, may be used.

If there exists such context parameter, then the keypad sequence monitor 312 displays a context cue that corresponds to such context parameter. For example, if a different drug concentration corresponds to lower and upper soft and hard limit values that define a range of valid treatment parameter values that include the sequence value, then the keypad sequence monitor 312 can provide an indicator to the user to suggest changing the drug concentration. The context cue, or indicator, may be provided as a visual indicator on the display, such as by highlighting the context parameter on the display (for example, see FIG. 3D). The method 700 returns to block 706, where the keypad sequence monitor 312 received a subsequent keypress.

If at block 706 either the initial or any subsequent keypress corresponds to a functional key, the method 700 proceeds to block 712. At block 712 the method 700 performs the function corresponding to the functional key. For example, the method 700 may receive a user input to program a treatment parameter value, select a context parameter, or perform any of the functions described above, or any other function for programming the infusion pump. The method 700 then ends at block 714.

In some embodiments, the method 700 also provides one or more keypad indicators in response to user keypresses. Providing such keypad indicators is described below with respect to FIG. 6. For example, in some embodiments, the method 700 performs the functions associated with updating keypad indicators as described below with respect to block 810. Such functions may be performed prior to, after, or concurrently with the displaying available context cues, as discussed above with respect to block 710.

Method of Displaying Keypad Indicators in Response to User Keypresses

Figure 6:
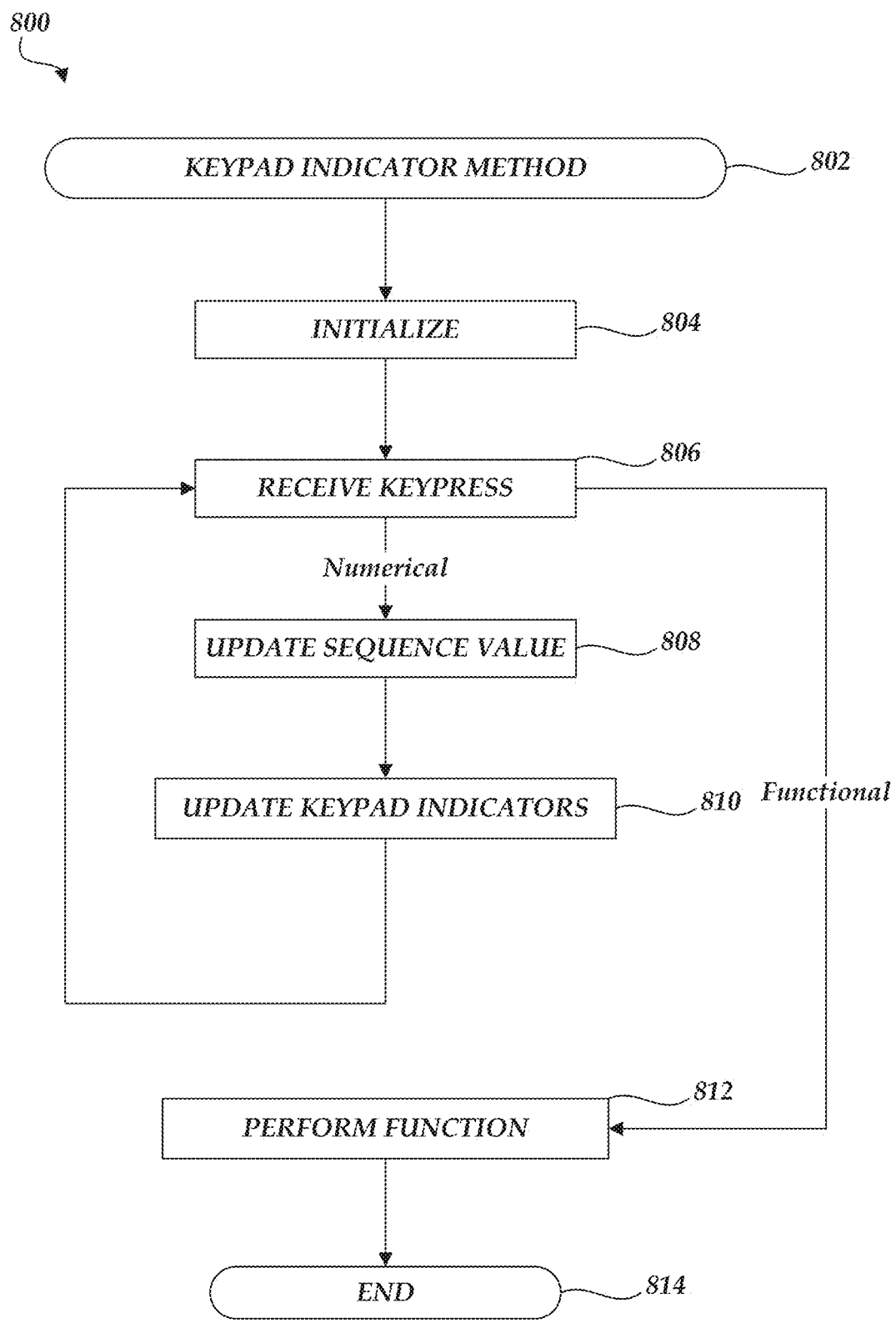
FIG. 6 illustrates an example keypad indicator display method in accordance with aspects of this disclosure.

With reference now to FIG. 6, an example keypad indicator display method 800 will be described. The example method 800 may be performed, for example, by the infusion pump 304 of FIGS. 2-3D (or one or more components thereof, such as the keypad sequence monitor 312). The method 800 illustrates an example algorithm that may be programmed, using any suitable programming environment or language, to create machine code capable of execution by a CPU or microcontroller of the infusion pump 304. Various embodiments may be coded using assembly, C, OBJECTIVE-C, C++, JAVA, or other human-readable languages and then compiled, assembled, or otherwise transformed into machine code that can be loaded into read-only memory (ROM), erasable programmable read-only memory (EPROM), or other recordable memory of the infusion pump 304 that is coupled to the CPU or microcontroller and then then executed by the CPU or microcontroller. For convenience, the steps of the example method 800 are described as being performed by the keypad sequence monitor 312 of infusion pump 304.

The method 800 begins at block 802. At block 804 the keypad sequence monitor 312 initializes memory and variables based upon selected context parameters. For example, the keypad sequence monitor 312 may select and access a particular drug library, or drug library portion, based upon selected context parameters. Such context parameters may include a selected clinical care area, drug for infusion, and drug concentration. Additional or alternative context parameters may be selected, as well. Context parameters may be selected by a user via a display and keypad, including, but not limited to, any of the displays and keypads of FIGS. 3A-3D.

Using the drug library and context parameters, the keypad sequence monitor 312 may determine lower and upper soft and hard limits to be used by the keypad sequence monitor 312. Such limits will be used by the keypad sequence monitor 312 to determine whether a sequence value entered by the user for a particular treatment parameter are within a valid range, and if not, whether relevant limits may be overridden, and whether any context cues are available for display, as discussed below.

At block 806 the keypad sequence monitor receives an initial keypress from the user. The keypress may correspond to a numerical value, such as any of the numerical values displayed on the keypad (e.g., 0-9, decimal point, and BACKSPACE or DELETE) or a functional key. Functional keys include context parameter selectors, fields into which data is to be entered by the user, and CANCEL or CONFIRM keys, as well as any other functional keys. One embodiment of such keys are illustrated above with respect to FIGS. 3A-3D.

If the keypress received by the keypad sequence monitor 312 is a numerical key, the method 800 proceeds to block 808, in which the entered sequence value is updated. For example, the sequence value is initially initialized to be blank. If the initially presses the key "2" then the keypad sequence monitor 312 updates the sequence value to be equal to the number 2. The method 800 proceeds to block 810.

At block 810, the method 800 determines whether to update one or more keypad indicators, such as by highlighting or changing the color of a portion of the keypad display or key. Examples of such actions are discussed above with respect to FIG. 3B and FIG. 3C (e.g., decimal point, "0" and BACKSPACE keys are highlighted in FIG. 3B, and decimal point and "0" keys are subsequently un-highlighted in FIG. 3C). For example, the keypad sequence monitor can determine whether a subsequent keypress will result in sequence value that is within a valid treatment parameter value range. As discussed above with respect to FIG. 3B, if the lower and upper soft limits are, for example, 2.5 and 20, and the user initially presses the "2" key, the keypad sequence monitor can determine that only subsequently pressing the decimal, "0" or BACKSPACE keys could result in a sequence value that is within the valid range defined by the currently-used lower and upper soft limit values.

In addition, if the keypad sequence monitor determines that the entered sequence value is outside of the range defined by the lower and upper soft limit values, but within the range defined by the lower and upper hard limit values, the keypad sequence monitor can provide one or more indicators that the user may override the soft limit restriction. For example, indicators such as indicators 534, 530 and key 532 (as illustrated and discussed with respect to FIG. 3C) may be displayed in response to such determination. The method 800 returns to block 806, where the keypad sequence monitor receives a subsequent keypress.

If at block 806 the either the initial or any subsequent keypress corresponds to a functional key, the method 800 proceeds to block 812. At block 812 the method 800 performs the method corresponding to the functional key. For example, the method 800 may receive a user input to program a treatment parameter value, select a context parameter, or perform any of the functions described above, or any other function for programming the infusion pump. The method 800 then ends at block 814.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. An infusion pump configured to provide one or more context cues to a user while the user programs the infusion pump to deliver an infusion therapy, the infusion pump comprising:
    a display configured to display a keypad and to receive input from a user via the keypad;
    a processor in communication with the display; and
    a memory in communication with the processor and configured to store instructions that when executed by the processor cause the execution of a keypad sequence monitor configured to:
        receive one or more context parameters, the context parameters corresponding to a drug selection, a drug concentration selection, or a clinical care area in which the drug is to be infused;
        access a drug library using the context parameters to determine lower and upper soft limit values and lower and upper hard limit values corresponding to the context parameters, wherein a valid treatment parameter range associated with a treatment parameter corresponds to a range of values between the lower and upper soft limit values;
        receive a keypress via the keypad;
        update a sequence value based upon the keypress;
        determine that the sequence value is outside of the valid treatment parameter range;
        determine that an updated context parameter different from the received context parameters is associated with updated lower and upper soft limit values that define an updated valid treatment parameter range for the treatment parameter that includes the sequence value; and
        display one or more context cues corresponding to the updated context parameter.

2. The infusion pump of claim 1, wherein the keypad sequence monitor is further configured to receive the one or more context parameters from the user via the keypad.

3. The infusion pump of claim 1, wherein the keypad sequence monitor is further configured to receive the one or more context parameters over a network.

4. The infusion pump of claim 1, wherein the drug library comprises the lower and upper soft and hard limit values.

5. The infusion pump of claim 1, wherein the drug library comprises lower and upper soft and hard limit values for each combination of context parameters.

6. The infusion pump of claim 1, wherein the keypress comprises a numerical value associated with the treatment parameter, and wherein the treatment parameter comprises one of a dose, an infusion rate, a volume to be infused, an infusion duration, or a patient weight.

7. The infusion pump of claim 1, wherein the keypad sequence monitor is further configured to determine that the sequence value is outside of the valid treatment parameter range prior to receiving a keypress that indicates that the user wishes to store and execute the infusion pump program.

8. The infusion pump of claim 7, wherein the keypress that indicates that the user wishes to store and execute the infusion pump program comprises an ENTER or RETURN keypress.

9. The infusion pump of claim 1, wherein the keypad sequence monitor is further configured to display the one or more context cues by altering the appearance of the displayed context parameter that corresponds to the updated context parameter.

10. The infusion pump of claim 1, wherein the keypad sequence monitor is further configured to update a keypad indicator in response to the received keypress, wherein the keypad indicator indicates which subsequent keypresses on the keypad would cause the sequence value to change and to become within the valid treatment parameter range.

11. A method of providing one or more context cues to a user while the user programs an infusion pump to deliver an infusion therapy, the method comprising:
    receiving one or more context parameters, the context parameters corresponding to a drug selection, a drug concentration selection, or a clinical care area in which the drug is to be infused;
    accessing a drug library using the context parameters to determine lower and upper soft limit values and lower and upper hard limit values corresponding to the context parameters, wherein a valid treatment parameter range associated with a treatment parameter corresponds to a range of values between the lower and upper soft limit values;
    receiving a keypress via a keypad displayed on the infusion pump;
    updating a sequence value based upon the keypress;
    determining that the sequence value is outside of the valid treatment parameter range;
    determining that an updated context parameter different from the received context parameters is associated with updated lower and upper soft limit values that define an updated valid treatment parameter range for the treatment parameter that includes the sequence value; and
    displaying one or more context cues corresponding to the updated context parameter.

12. The method of claim 11, wherein receiving the one or more context parameters comprises receiving the one or more context parameters from the user via the keypad.

13. The method of claim 11, wherein receiving the one or more context parameters comprises receiving the one or more context parameters over a network.

14. The method of claim 11, wherein the drug library comprises the lower and upper soft and hard limit values.

15. The method of claim 11, wherein the drug library comprises lower and upper soft and hard limit values for each combination of context parameters.

16. The method of claim 11, wherein the keypress comprises a numerical value associated with the treatment parameter, and wherein the treatment parameter comprises one of a dose, an infusion rate, a volume to be infused, an infusion duration, or a patient weight.

17. The method of claim 11, further comprising determining that the sequence value is outside of the valid treatment parameter range prior to receiving a keypress that indicates that the user wishes to store and execute the infusion pump program.

18. The method of claim 17, wherein the keypress that indicates that the user wishes to store and execute the infusion pump program comprises an ENTER or RETURN keypress.

19. The method of claim 11, wherein displaying the one or more context cues comprises altering the appearance of the displayed context parameter that corresponds to the updated context parameter.

20. The method of claim 11, further comprising updating a keypad indicator in response to the received keypress, wherein the keypad indicator indicates which subsequent keypresses on the keypad would cause the sequence value to change and to become within the valid treatment parameter range.

* * * * *